United States Patent
Cason et al.

(10) Patent No.: US 11,379,660 B2
(45) Date of Patent: Jul. 5, 2022

(54) DEEP LEARNING APPROACH TO COMPUTING SPANS

(71) Applicant: International Business Machines Corporation, Armonk, NY (US)

(72) Inventors: Joshua Cason, Oxford, NC (US); Chris Mwarabu, Holly Springs, NC (US); Thomas Hay Rogers, Durham, NC (US); Corville O. Allen, Morrisville, NC (US)

(73) Assignee: International Business Machines Corporation, Armonk, NY (US)

( * ) Notice: Subject to any disclaimer, the term of this patent is extended or adjusted under 35 U.S.C. 154(b) by 327 days.

(21) Appl. No.: 16/454,311

(22) Filed: Jun. 27, 2019

(65) Prior Publication Data
US 2020/0410050 A1    Dec. 31, 2020

(51) Int. Cl.
*G06F 40/205* (2020.01)
*G06N 20/00* (2019.01)
*G16H 50/20* (2018.01)
*G06F 40/279* (2020.01)

(52) U.S. Cl.
CPC .......... *G06F 40/205* (2020.01); *G06F 40/279* (2020.01); *G06N 20/00* (2019.01); *G16H 50/20* (2018.01)

(58) Field of Classification Search
CPC ..... G06F 40/205; G06F 40/279; G16H 50/20; G06N 20/00; G06N 20/10; G06N 20/20
See application file for complete search history.

(56) References Cited

U.S. PATENT DOCUMENTS

| | | | |
|---|---|---|---|
| 6,574,633 B1 | 6/2003 | Jamalabad | |
| 9,471,559 B2* | 10/2016 | Castelli | G06F 16/353 |
| 9,715,495 B1* | 7/2017 | Tacchi | G06F 16/358 |
| 9,715,662 B2 | 7/2017 | Carmeli | |
| 2014/0163955 A1* | 6/2014 | Ng Tari | G06F 40/205 |
| | | | 704/9 |
| 2017/0270052 A1* | 9/2017 | Brown | G06F 9/30105 |

(Continued)

FOREIGN PATENT DOCUMENTS

| | | | |
|---|---|---|---|
| CN | 106484674 A | 3/2017 | |
| CN | 108304387 A * | 7/2018 | G06F 40/284 |

(Continued)

OTHER PUBLICATIONS

Jin (CN 108304387) Official Translation enclosed.*

(Continued)

*Primary Examiner* — Fariba Sirjani
(74) *Attorney, Agent, or Firm* — Grant M. McNeilly

(57) ABSTRACT

A method, system, and computer program product for using a natural language processor is disclosed. Included are importing highlighted and non-highlighted training text each including training nodes, one-hot encoding the training text, training a projection model using the training text, processing the highlighted training text using the projection model, and training a classifier model using the highlighted processed training text. Also included are importing new text (Continued)

including new nodes, one-hot encoding the new text, processing the new text using the projection model, and determining, using the classifier model, whether one of the new nodes is in a sought-after class.

25 Claims, 11 Drawing Sheets

(56) References Cited

U.S. PATENT DOCUMENTS

| | | | |
|---|---|---|---|
| 2017/0286835 A1* | 10/2017 | Ho | G06N 3/08 |
| 2017/0300632 A1 | 10/2017 | Bai | |
| 2017/0372696 A1* | 12/2017 | Lee | G10L 15/16 |
| 2018/0075011 A1* | 3/2018 | Allen | G06F 40/242 |
| 2018/0101598 A1* | 4/2018 | Allen | G06F 40/268 |
| 2018/0150607 A1 | 5/2018 | Macleod | |
| 2019/0057191 A1 | 2/2019 | Bao | |

FOREIGN PATENT DOCUMENTS

| | | | | |
|---|---|---|---|---|
| CN | 109062901 A | * | 12/2018 | G06F 12/023 |
| CN | 109416674 A | * | 3/2019 | G06F 12/023 |

OTHER PUBLICATIONS

Chazal et al., "An Introduction to Topological Data Analysis: Fundamental and Practical Aspects for Data Scientists," arXiv:1710.04019 [math.ST], Oct. 11, 2017, pp. 1-38.

Jia et al., "Improved Discourse Parsing with Two-Step Neural Transition-Based Model," ACM Trans. Asian Low-Resour. Lang. Inf. Process., vol. 17, No. 2, Article 11, Jan. 2018, pp. 1-21.

Sporleder et al., "Discourse Chunking and Its Application to Sentence Compression," Proceedings of Human Language Technology Conference and Conference on Empirical Methods in Natural Language Processing (HLT/EMNLP), Oct. 2005, pp. 257-264.

Van Den Berg et al., "Topological and Simplicial Models of Identity Types," ACM Trans. Comput. Logic 13, 1, Article 3, Jan. 2012, 44 pages.

Young et al., "Recent Trends in Deep Learning Based Natural Language Processing," IEEE Computational Intelligence Magazine, Jul. 18, 2018, pp. 55-75.

International Search Report and Written Opinion dated Sep. 27, 2020, for International Application No. PCT/IB2020/055332, filed Jun. 5, 2020.

* cited by examiner

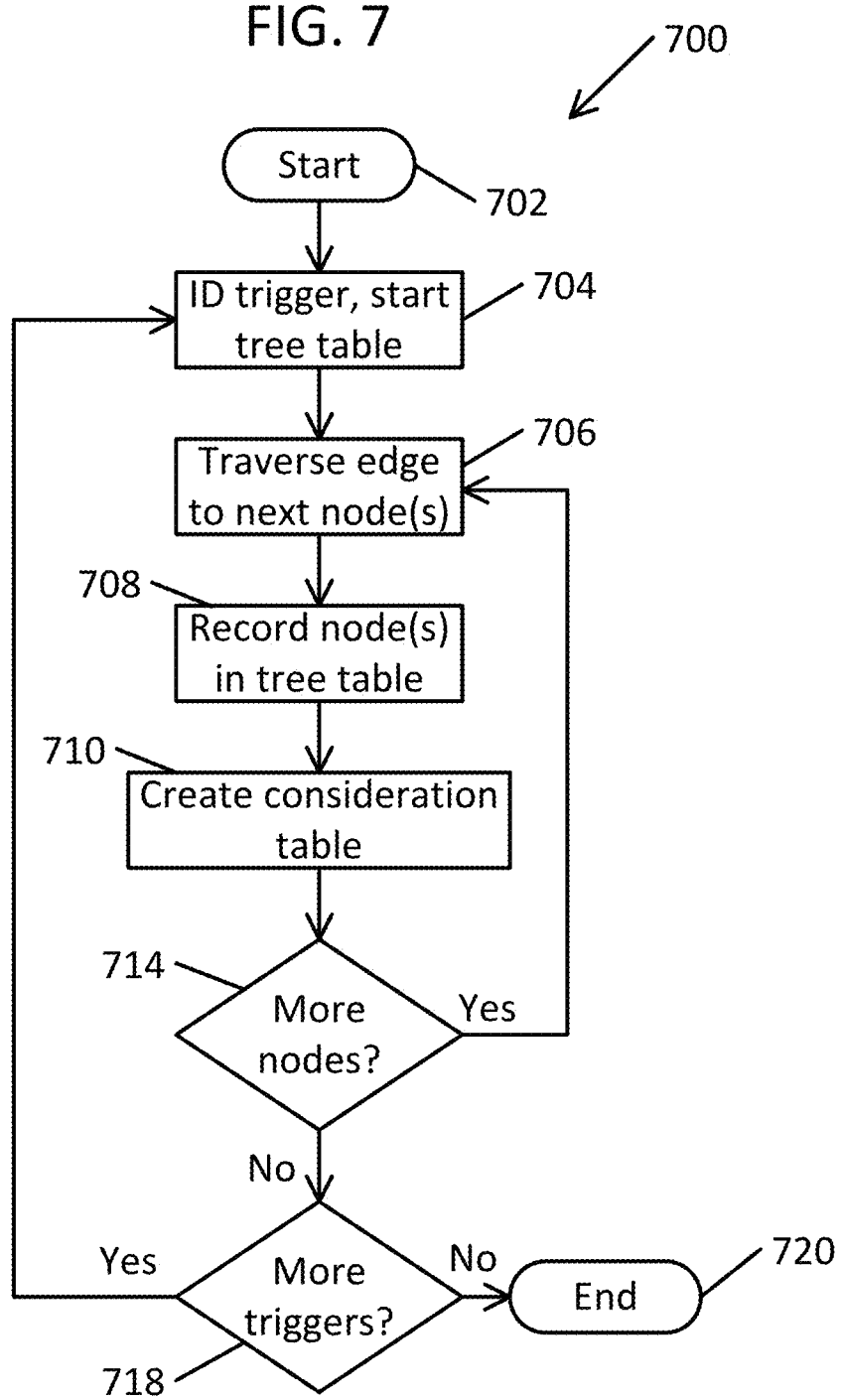

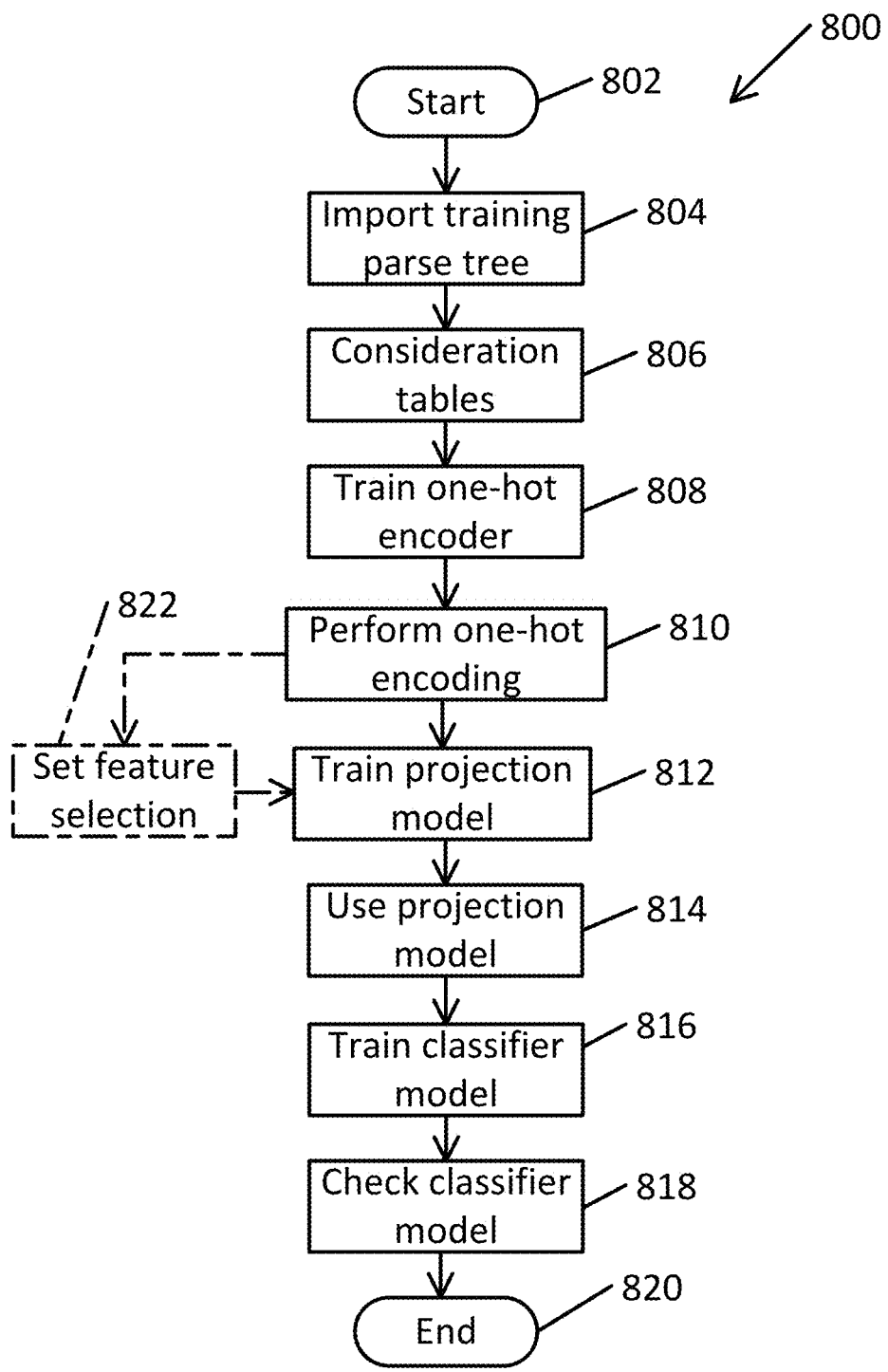

DEEP LEARNING APPROACH TO COMPUTING SPANS

BACKGROUND

The present application relates generally to an improved data processing apparatus and method and more specifically to mechanisms for providing an approach to machine learning of hypothetical statements in texts such as medical text, judicial statements, and other corpora of textual documents.

Decision-support systems exist in many different industries where human experts require assistance in retrieving and analyzing information. An example that will be used throughout this application is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. As development progressed, more sophisticated probabilistic reasoning capability was added, and then systems using unstructured knowledge started to appear. More recently, clinical decision rules have been developed for a number of medical disorders, and computer systems have been developed to help practitioners and patients apply these rules.

SUMMARY

According to some embodiments of the present disclosure, a method, system, and computer program product for using a natural language processor is disclosed. Included are importing highlighted and non-highlighted training text each including training nodes, one-hot encoding the training text, training a projection model using the training text, processing the highlighted training text using the projection model, and training a classifier model using the highlighted processed training text. Also included are importing new text including new nodes, one-hot encoding the new text, processing the new text using the projection model, and determining, using the classifier model, whether one of the new nodes is in a sought-after class.

According to some embodiments of the present disclosure, a method and system of training a natural language processor is disclosed. Included are importing highlighted training text each including training nodes, converting the training text into training conversion tables, training a one-hot encoder using the training conversion tables, and one-hot encoding the training conversion tables to generate training vectors. Also included are training a projection model using the training vectors, processing the highlighted training vectors using the projection model to generate highlighted processed training vectors, and training a classifier model using the highlighted processed training vectors, wherein the classifier model determines whether a node is in a sought-after class.

BRIEF DESCRIPTION OF THE DRAWINGS

FIG. 7 is a flowchart of an example method of finding a span of a parse tree data structure.

FIG. 8 is a flowchart of a method of using a parse tree to train a natural language processing (NLP) system to operate on natural language text.

DETAILED DESCRIPTION

Figure 1:
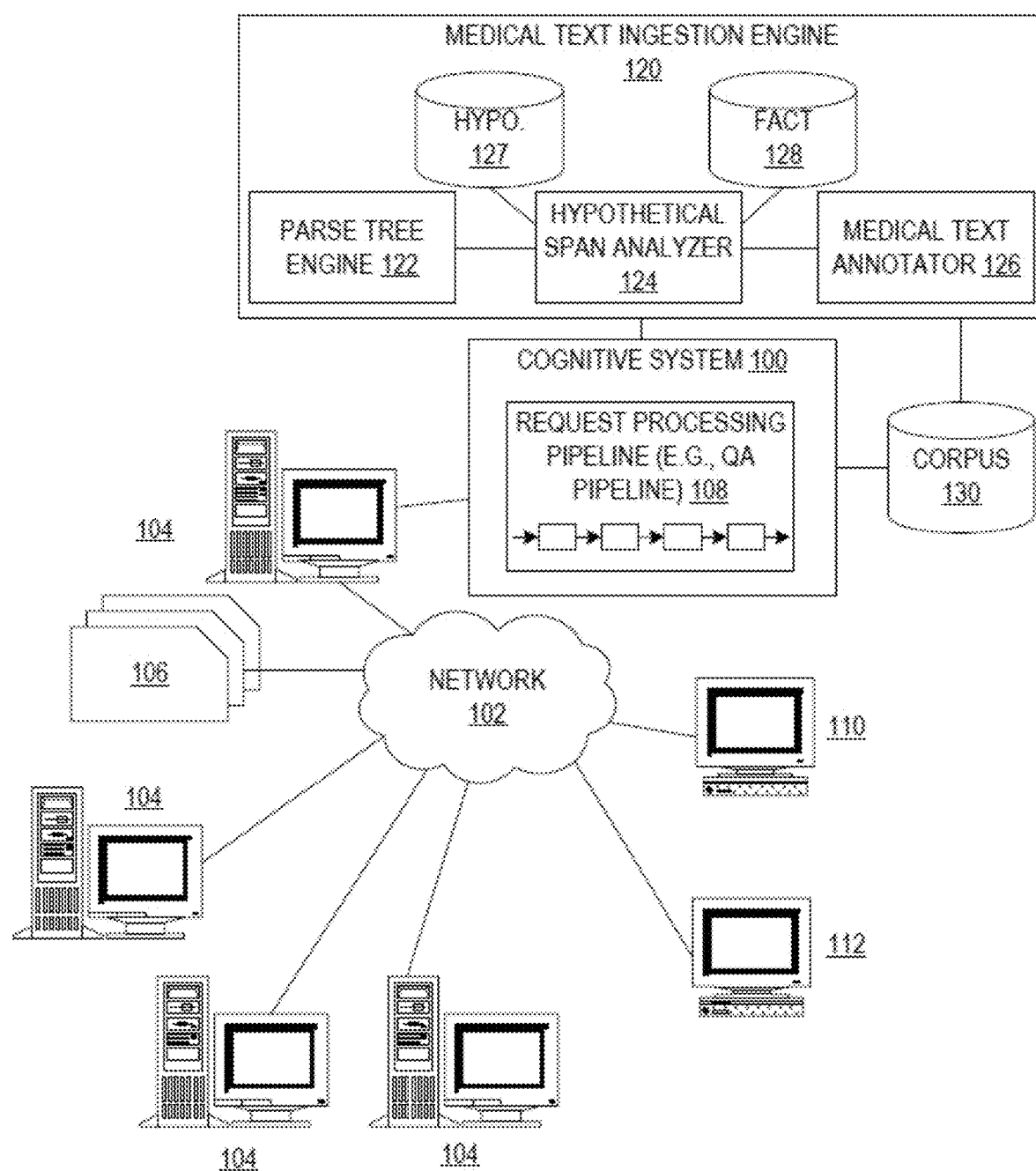
FIG. 1 depicts a schematic diagram of one illustrative embodiment of a cognitive healthcare system in a computer network.

When performing natural language processing of portions of text, such as medical texts, judicial texts, and the like, it is often important to be able to distinguish portions of text that are directed to actual factual statements and portions of text that include hypothetical descriptions. For example, in the case of medical texts and natural language processing performed in order to facilitate treatment of a patient, it is often crucial to be able to distinguish actual events that are important for more accurate treatment suggestions from hypothetical portions of text that may represent possibilities which may lead to erroneous diagnosis and treatment of the patient. Most of the time, medical notes contain both facts describing what actually happened, and plans (a.k.a. hypotheticals) which indicate what was discussed with the patient but did not in fact happen. For example, a patient's electronic medical record (EMR) may have laboratory reports indicating that a particular laboratory test was performed, and specific results were obtained from the laboratory test. This would be an example of an actual factual event occurring with regard to the patient. In addition, the doctor may have their own notes in the patient's EMR indicating potential procedures or events that the doctor discussed with the patient (e.g., "We recommended that the patient have a mammogram performed."). Such potential procedures or events did not actually happen but represent potential plans for the patient. While items were discussed with the patient, they are in fact hypothetical in nature since it is not known, at the time, whether the procedure or event will occur.

For a cognitive system, such as the IBM Watson® cognitive system available from International Business Machines Corporation of Armonk, N.Y., actual facts are often the most important part of such medical texts since the treatment recommendations are based on actual events and facts. However, the planned actions or non-implemented actions, possible events, and the like (i.e., hypotheticals) may also be documented in the medical text even though they do not yet represent actual events or facts. In order to increase the accuracy of such cognitive systems, it would be beneficial to be able to distinguish portions of textual content representing hypotheticals from portions of textual content representing actual facts and events. Thereby, the treatment recommendations generated by the cognitive system will be based on the portions representing actual facts and events.

The illustrative embodiments provide mechanisms for ingesting electronic texts, documents, or other portions of textual content and analyzing the textual content to distinguish portions of the text directed to hypotheticals from portions of text directed to actual facts or events that actually occurred. For purposes of the following description, illustrative embodiments will be provided that are directed to an implementation in the context of medical texts and a cognitive medical treatment recommendation system. However, such example embodiments are not to be taken in a limiting context. In particular, it should be appreciated that various other embodiments may be implemented with regard to any types of text of various domains other than medical texts without departing from the spirit and scope of the present invention. Thus, for example, the mechanisms described hereafter may be implemented with regard to judicial text or any other type of text which may include hypothetical portions and factual portions and where the distinguishing between hypothetical portions and factual portions of text is subsequently used to perform an analytical, cognitive, or other processing of the text to generate a result.

In the context of a medical treatment recommendation system embodiment in which the mechanisms of the illustrative embodiments distinguish factual portions of text from hypothetical portions of text, the mechanisms of the illustrative embodiments may ingest various types of medical texts and apply the mechanisms of the illustrative embodiments to these medical texts. These medical texts may include, for example, patient electronic medical records (EMRs) in which medical service providers (e.g., doctors, nurses, hospitals, medical laboratories, pharmacies, and medical insurance companies) may contribute content for inclusion in the EMR. As such, the medical text from each of these sources may contain both facts (e.g., actual occurrences, events, or results) and hypotheticals (e.g., plans or other possibilities that did not in actuality occur).

In some instances, a single statement or medical text may contain both facts and hypotheticals, such as in the example statement, "Given her node positivity and lack of comorbidities, we recommend neoadjuvant therapy." In such a case, while making a treatment recommendation for a patient, it is desirable to know the fact that the patient has node positivity and a lack of comorbidities. However, it is also crucial for the treatment recommendation system to know that the patient has not actually undergone neoadjuvant therapy rather than interpret this portion of the statement as factual as well. Rather than the system thinking that the patient has actually undergone neoadjuvant therapy, the system should be able to determine that this portion of the statement is referring to a recommendation of a future plan (i.e., a hypothetical) rather than a fact of an event that occurred. Thus, the system can ignore this portion of the statement or simply treat this portion differently from the rest of the statement.

In order to distinguish portions of medical text that are describing actual facts from portions of text that are directed to hypotheticals, the illustrative embodiments provide mechanisms implementing a generalizable approach that does not make assumptions of sentence structure. The illustrative embodiments utilize two sets of dictionary data structures. The first is a set of dictionary data structures directed to identifying terms and phrases corresponding to hypothetical portions of content which a medical treatment recommendation cognitive system may ignore when performing medical treatment recommendation analysis. The second is a second set of dictionary data structures directed to distinguishing terms and phrases associated with factual portions of content which should be used as a basis for performing such medical treatment recommendation analysis. In addition, parse trees are utilized that include an enhanced representation of textual content against which the dictionaries are applied. A span of an annotation (e.g., hypothetical or factual annotation) is determined by looking at the sub-tree rooted by a matching dictionary entry. For example, if a node of the parse tree matches a hypothetical term or phrase in the hypothetical dictionary data structures, then the sub-tree rooted by the matching hypothetical term or phrase may be annotated to be hypothetical. The approach implemented by the mechanisms of the illustrative embodiments is easy to tune for previously unseen cases, such as by means of different or updated dictionaries of hypothetical terms/phrases.

The illustrative embodiments may operate in a backend portion of the medical treatment recommendation system where the natural language processing of medical texts is performed. In the backend system, the medical texts can be analyzed using several natural language processing models including one or more models implementing one or more illustrative embodiments of the present disclosure. The result of such analysis is a set of annotated medical texts that may be utilized by the medical treatment recommendation cognitive system both with regard to machine learning and with regard to actual application to specific patient EMRs for providing specific patient medical treatment recommendations.

Before beginning the discussion of the various aspects of the illustrative embodiments in more detail, it should first be appreciated that throughout this description the term "mechanism" will be used to refer to elements of the present disclosure that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present disclosure and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the disclosure, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following disclosure uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to a person having ordinary skill in the art in view of the present disclosure that there are many other alternative implementations for these various elements that may be utilized in addition to, or in replacement of, the examples provided herein without departing from the spirit and scope of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present disclosure provides mechanisms for analyzing medical texts and distinguishing hypothetical portions of text from factual portions of text, as well as annotating such portions of text so that they may be included or excluded from further consideration by the medical treatment recommendation cognitive system when performing its machine learning and/or medical treatment recommendation operations. The mechanisms of the illustrative embodiments improve the accuracy of the medical treatment recommendation cognitive system by informing the system of what portions the system can accurately rely on as indicative of actual facts as opposed to potential facts (i.e. hypotheticals) that cannot be relied upon. In this way the medical treatment recommendation cognitive system is able to base its final medical treatment recommendations on the factual events and not be erroneously affected by the hypothetical portions of medical text.

The mechanisms of the illustrative embodiments utilize a hybrid approach that involves both the use of specially constructed sets of dictionary data structures as well as parse tree data structures. The specially constructed sets of dictionary data structures comprise a set of hypothetical dictionary data structures that specify terms or phrases that are indicative of hypothetical portions of content, with these terms or phrases in the set of hypothetical dictionary data structures being referred to herein as "ignore triggers". The specially constructed sets of dictionary data structures further comprise a set of factual dictionary data structures that specify terms or phrases that are indicative of factual portions of content, with these terms or phrases in the set of factual dictionary data structures being referred to herein as "confirm triggers". The ignore triggers and confirm triggers are combined with a systemic view of a portion of textual content (e.g., a document, paragraph, sentence, phrase, etc.) obtained from a parse tree, which enables a more generalizable approach.

The combination of the ignore and confirm triggers with the parse trees allows for portions of the parse trees to be identified as corresponding to hypothetical portions of content, also referred to herein as "hypothetical spans", and other portions of the parse trees as being associated with factual portions of content, also referred to herein as "factual spans". These various spans may be annotated as hypothetical or factual, respectively, in metadata associated with these portions of content. The annotated spans or portions of the content may then be processed by the medical treatment recommendation cognitive system so as to ignore the portions of content corresponding to hypothetical spans (e.g., zero weightings may be applied to these portions of content or logic may be provided for providing other evaluation of the information in hypothetical spans as plans of medical professionals). In some illustrative embodiments, the annotations contained within hypothetical spans could be removed so as to generate a pruned parse tree which is provided to the medical treatment recommendation cognitive system for use in performing its treatment recommendation cognitive operations. In still other illustrative embodiments, rather than giving the hypothetical spans zero weight or pruning these spans from the parse tree, a relatively lower weight may be given to the annotations inside these spans than to annotations within factual spans so as to still allow some influence from the hypothetical spans to be provided but mitigating their influence by weighting them relatively lower.

Thus, rather than these portions of content being considered by the medical treatment recommendation cognitive system as representing evidence upon which the medical treatment recommendation cognitive system may base its treatment recommendations and thereby potentially generate erroneous medical treatment recommendations, the medical treatment recommendation cognitive system may instead recognize these portions as not being indicative of facts associated with the patient. Rather, they are considered potential facts that are not indicative of the patient's current status and cannot be relied upon, or can be relied upon with less confidence. To the contrary, in some illustrative embodiments, the medical treatment recommendation cognitive system performs its operations only on the portions of content corresponding to the factual spans. In other illustrative embodiments, while the hypothetical spans may still be considered, their relative lack of trustworthiness may be quantified by providing a relatively lower weight or significance to the information obtained from these hypothetical spans than other factual spans.

Figure 2:
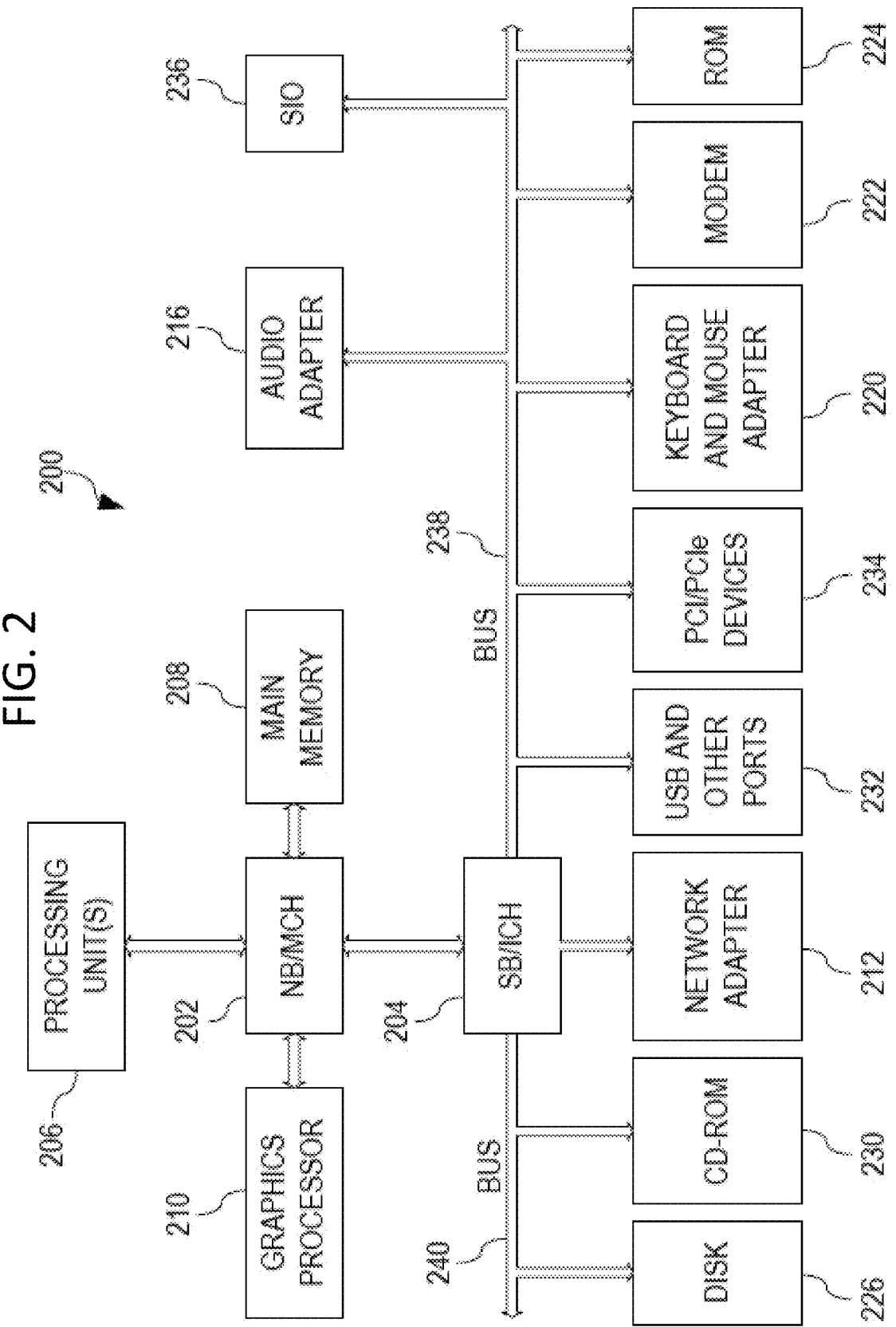
FIG. 2 is a block diagram of an example data processing system in which aspects of the illustrative embodiments are implemented.
Figure 3:
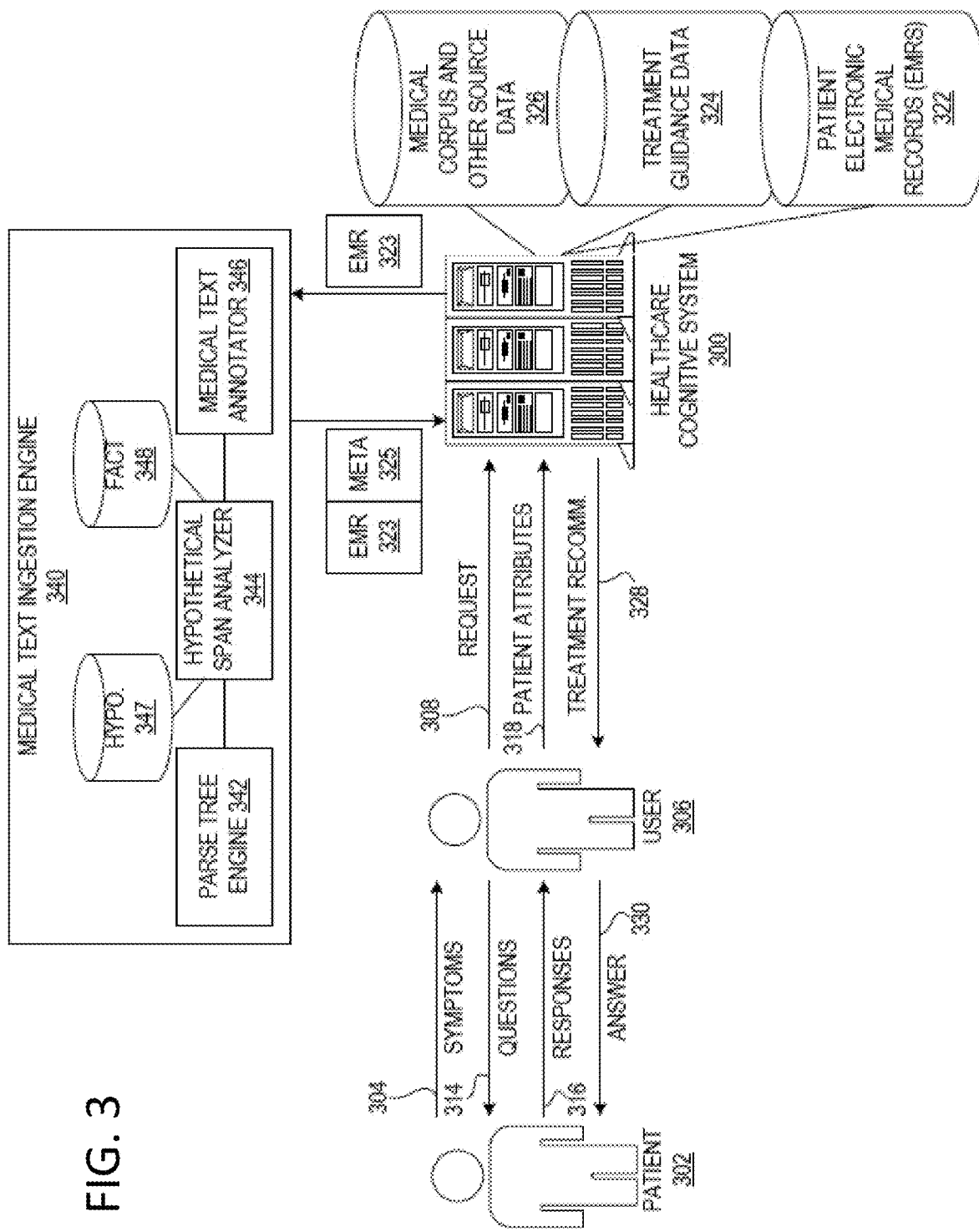
FIG. 3 is an example diagram illustrating an interaction of elements of a healthcare cognitive system in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline), a request processing methodology, and a request processing computer program product with which the mechanisms of the illustrative embodiments are implemented. These requests may be provided as structured or unstructured request messages, natural language questions, or any other suitable format for requesting an operation to be performed by the healthcare cognitive system. As described in more detail hereafter, the particular healthcare application that is implemented in the example cognitive system of embodiments of the present invention is a healthcare application for providing medical treatment recommendations and thus, the healthcare cognitive system may also be referred to as a medical treatment recommendation cognitive system herein.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline) depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have their own associated corpus or corpora that they ingest and operate on (e.g., one corpus for blood disease domain documents and another corpus for cancer diagnostics domain related documents in the above examples). In some cases, the request processing pipelines may each operate on the same domain of input questions but may have different configurations (e.g., different annotators or differently trained annotators, such that different analysis and potential answers are generated). The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while embodiments of the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of, "What diagnosis applies to patient P?", the cognitive system may instead receive a request of, "generate diagnosis for patient P," or the like. It should be appreciated that the mechanisms of the QA system pipeline may operate on requests in a similar manner to that of input natural language questions with minor modifications. In some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline (or request processing pipeline) mechanisms of a healthcare cognitive system with regard to annotating ingested medical texts and operating on these ingested medical texts. Thereby, healthcare-based operations can be performed that distinguish between hypothetical portions of medical text and factual portions of medical texts. In particular, in some illustrative embodiments, the medical texts may comprise patient EMRs and the healthcare-based operations may comprise providing a medical treatment recommendation based on the EMRs of a patient. In this way, the healthcare cognitive system provides a decision support system directed to medical treatment recommendations.

In view of the above, it is important to first have an understanding of how cognitive systems, and question and answer creation in a cognitive system implementing a QA pipeline, is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation (e.g., items of interest to a particular user, potential new contact recommendations, or the like).

IBM Watson® is an example of one such cognitive system which can process human readable language and identify inferences between text passages with human-like high accuracy at speeds far faster than human beings and on a larger scale. In general, such cognitive systems are able to perform, but are not limited to, one or more of the following functions:

navigate the complexities of human language and understanding;

ingest and process vast amounts of structured and unstructured data;

generate and evaluate hypotheses;

weigh and evaluate responses that are based only on relevant evidence;

provide situation-specific advice, insights, and guidance;

improve knowledge and learn with each iteration and interaction through machine learning processes;

enable decision making at the point of impact (e.g., contextual guidance);

scale in proportion to the task;

extend and magnify human expertise and cognition;

identify resonating, human-like attributes and traits from natural language;

deduce various language-specific or agnostic attributes from natural language;

recollect, with a high degree of relevancy, from data points (images, text, voice) (e.g., memorization and recall);

predict and sense with situational awareness that mimics human cognition based on experiences; and answer questions based on natural language and specific evidence;

In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area (e.g., financial domain, medical domain, legal domain, etc.) where the body of knowledge (knowledgebase) can be organized in a variety of configurations (e.g., a structured repository of domain-specific information, such as ontologies, or unstructured data related to the domain, or a collection of natural language documents about the domain).

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline (e.g., sending the query to the QA pipeline as a well-formed question which is then interpreted by the QA pipeline and a response is provided containing one or more answers to the question). Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis (e.g., comparisons, natural language analysis, lexical analysis, or the like) and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response (i.e. candidate answer) is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers (i.e. candidate answers).

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions (such as in terms of roles, type of information, tasks, or the like, associated with the question) in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers (i.e. candidate answers, for the input question). The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present disclosure, it will be assumed that the request processing pipeline 108 is implemented as a QA pipeline that operates on structured and/or unstructured requests in the form of input questions. The cognitive system 100 is implemented on one or more computing devices 104 (comprising one or more processors and one or more memories, and potentially any other computing device elements generally known in the art including buses, storage devices, communication interfaces, and the like) connected to the computer network 102. The network 102 includes multiple computing devices 104 in communication with each other and with other devices or components via one or more wired and/or wireless data communication links, where each communication link comprises one or more of wires, routers, switches, transmitters, receivers, or the like. The cognitive system 100 and network 102 enables question processing and answer generation (QA) functionality for one or more cognitive system users via their respective computing devices 110-112. Other embodiments of the cognitive system 100 may be used with components, systems, sub-systems, and/or devices other than those that are depicted herein.

The cognitive system 100 is configured to implement a QA pipeline 108 that receives inputs from various sources. For example, the cognitive system 100 receives input from the network 102, a corpus of electronic documents 106, cognitive system users (not shown), and/or other data and other possible sources of input. In one embodiment, some or all of the inputs to the cognitive system 100 are routed through the network 102. The various computing devices 104 on the network 102 include access points for content creators and QA system users. Some of the computing devices 104 include devices for a database storing the corpus of data 106 (which is shown as a separate entity in FIG. 1 for illustrative purposes only). Portions of the corpus of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global (e.g., the Internet).

In one embodiment, the content creator creates content in a document of the corpus of data 106 for use as part of a corpus of data with the cognitive system 100. The document includes any file, text, article, or source of data for use in the cognitive system 100. QA system users access the cognitive system 100 via a network connection or an Internet connection to the network 102, and input questions to the cognitive system 100 that are answered by the content in the corpus of data 106. In one embodiment, the questions are formed using natural language. The cognitive system 100 parses and interprets the question via a QA pipeline 108, and provides a response to the cognitive system user (e.g., via cognitive system user device 110) containing one or more answers to the question. In some embodiments, the cognitive system 100 provides a response to users in a ranked list of candidate answers while in other illustrative embodiments, the cognitive system 100 provides a single final answer or a combination of a final answer and ranked listing of other candidate answers.

The cognitive system 100 implements the QA pipeline 108 which comprises a plurality of stages for processing an input question and the corpus of data 106. The QA pipeline 108 generates answers for the input question based on the processing of the input question and the corpus of data 106. The QA pipeline 108 will be described in greater detail hereafter with regard to FIG. 3.

In some illustrative embodiments, the cognitive system 100 may be the IBM Watson® cognitive system available from International Business Machines Corporation of Armonk, N.Y., which is augmented with the mechanisms of the illustrative embodiments described hereafter. As outlined previously, a QA pipeline of the IBM Watson® cognitive system receives an input question which it then parses to extract the major features of the question, which in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question. The QA pipeline of the IBM Watson® cognitive system then performs deep analysis on the language of the input question and the language used in each of the portions of the corpus of data found during the application of the queries using a variety of reasoning algorithms.

The scores obtained from the various reasoning algorithms are then weighted against a statistical model that summarizes a level of confidence that the QA pipeline of the IBM Watson® cognitive system has regarding the evidence that the potential response (i.e. candidate answer) is inferred by the question. This process is repeated for each of the candidate answers to generate ranked listing of candidate answers which may then be presented to the user that submitted the input question, or from which a final answer is selected and presented to the user. More information about the QA pipeline of the IBM Watson® cognitive system may be obtained, for example, from the IBM Corporation website, IBM Redbooks, and the like. For example, information about the QA pipeline of the IBM Watson® cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited as such. Rather, the input question may in fact be formatted or structured as any suitable type of request which may be parsed and analyzed using structured and/or unstructured input analysis, including, but not limited to, the natural language parsing and analysis mechanisms of a cognitive system such as IBM Watson®, to determine the basis upon which to perform cognitive analysis and providing a result of the cognitive analysis. In the case of a healthcare based cognitive system, this analysis may involve processing patient EMRs, medical guidance documentation from one or more corpora, and the like, to provide a healthcare oriented cognitive system result.

In the context of the present disclosure, cognitive system 100 may provide a cognitive functionality for assisting with healthcare-based operations. For example, depending upon the particular implementation, the healthcare-based operations may comprise patient diagnostics, medical treatment recommendation systems, medical practice management systems, personal patient care plan generation and monitoring, patient EMR evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like.

In one illustrative embodiment, the cognitive system 100 is a medical treatment recommendation system that analyzes a patient's EMR in relation to medical guidelines and other medical documentation in a corpus or corpora of information to generate a medical treatment recommendation as to how to treat a medical malady or condition of the patient. In other illustrative embodiments, the domain may be a judicial domain with the cognitive system 100 providing cognitive analysis of hypotheticals and factual statements regarding legal cases and legal text. For example, the cognitive system 100 may provide recommendations based on distinguishing hypotheticals in victim, witness, or accused records, statements, and the like. For example, the statements, "The victim's phone was in the car. We believe the victim placed her phone in the car" may be analyzed using the mechanisms of the illustrative embodiment to distinguish the fact that the victim's phone was in the car from the hypothetical that the victim himself/herself actually placed the phone in the car. Recommendations or other cognitive or algorithm operations may then be performed based on the distinguishing of factual portions from hypothetical portions.

As shown in FIG. 1, and again with reference to a medical treatment recommendation cognitive system implementation, the cognitive system 100 is further augmented, in accordance with the mechanisms of the illustrative embodiments, to include logic implemented in specialized hardware, software executed on hardware, or any combination of specialized hardware and software executed on hardware, for implementing a medical text ingestion engine 120, which can be accomplished, for example, using server 104. The medical text ingestion engine 120 itself implements a parse tree engine 122, hypothetical span analyzer 124, and medical text annotator 126. Moreover, the hypothetical span analyzer 124 has associated hypothetical dictionary data structures 127 and factual dictionary data structures 128 that the hypothetical span analyzer 124 utilizes to identify hypothetical and factual spans within a parse tree, as described hereafter.

The medical text ingestion engine 120 may operate on any medical textual content present in the corpus 130 and operates on this medical text go annotate the medical text as part of an ingestion operation. The ingestion operation generates an in-memory representation of the medical text for use by the cognitive system 100 when performing its cognitive operations, such as a healthcare based cognitive operation utilizing pipeline 108. These medical texts may include medical guideline documents, medical position papers, health insurance guidelines, or any other medical information in which factual and/or hypothetical statements may be present. In some illustrative embodiments, the medical texts in corpus 130 may comprise a patient registry having patient EMRs for one or more patients stored therein. These patient EMRs may comprise information obtained from a variety of different sources of medical information for the patients including doctor generated EMRs, institution generated EMRs (such as from a medical practice, hospital, urgent care facility, etc.), pharmacy generated records, medical laboratory records, and the like. This information may be compiled together into an EMR for the patient or set of EMRs for the patient. Alternatively, this information may be separately stored in separate data structures associated with an identifier of the patient.

The medical texts, as noted above, may comprise both factual and hypothetical portions of content. The medical text ingestion engine 120 operates to retrieve such medical texts from the corpus 130, such as in response to a received request or as part of a general ingestion operation occurring prior to the receipt of a specific request. For example, the cognitive system 100 may receive a request to generate a medical treatment recommendation for a specified patient. In response, the cognitive system 100 may request that the medical text ingestion engine 120 ingest the specified patient's EMRs from the corpus 130. Alternatively, a plurality of EMRs for a plurality of patients in the patient registry of the corpus 130 may be ingested as part of an initialization or periodic process of the medical text ingestion engine 120. In either case, the medical text ingestion engine 120 operates on the medical text of the patient EMRs, or other medical texts as the case may be, to distinguish between hypothetical portions of content (hypothetical statements or phrases) in the medical text and factual portions of content. The medical text is annotated accordingly by adding annotations to the metadata associated with the medical text. The annotated medical text may be provided to the cognitive system 100 as an in-memory representation of the medical text upon which the cognitive system 100 may perform its cognitive operations.

In order to generate the annotated medical text, the medical text is received or retrieved by the medical text ingestion engine 120 from the corpus 130. The medical text is then parsed by the parse tree engine 122 using logical parsing techniques to generate a parse tree. Regardless of the particular parsing techniques utilized by the parse tree engine 122, the resulting parse tree data structures, generated by the parse tree engine 122 based on the analysis of the medical text, provide structural representations of portions of textual content in the medical texts (e.g., sentences in the medical text). The parse tree provides a hierarchical visualization of the portion of textual content (e.g., sentence) enabling the inferring of relationships between tokens (i.e. words or phrases corresponding to nodes of the parse tree).

The hypothetical span analyzer 124 implements a hybrid technique for searching the parse tree data structure for tokens matching ignore triggers or confirm triggers specified in the hypothetical dictionary data structures 127 (ignore triggers) and factual dictionary data structures 128 (confirm triggers). The hypothetical dictionary data structures 127 specify those terms and phrases that are indicative of a hypothetical statement or hypothetical portion of a statement. The factual dictionary data structures 128 specify those terms and phrases that are indicative of a factual statement or portion of a statement. Again, a hypothetical is an indication of something that has not actually occurred, such as an action, event, designation of state or condition, or other potential occurrence that has not in fact actually occurred. A fact, on the other hand, is something that has actually happened (i.e. an event, action, designation of state or condition, or other type of occurrence that has actually occurred). In the context of medical texts, hypotheticals often times are associated with future plans or potential conditions/outcomes associated with a patient's treatment that may or may not later occur. On the other hand, facts are associated with the current or past condition of the patient, current or past procedures performed on the patient, and other patient condition or state information and event information that actually occurred.

For example, the hypothetical dictionary data structure 127 may include an entry that identifies the term "discussed" as an ignore trigger. That is, in the context of this example, it has been determined that the term "discussed" when used in medical texts, such as a patient's EMR, indicates a potential future event since it often refers to the doctor discussing with the patient possible treatments or possible conditions or states of the patient that did not in fact happen yet (e.g., "I discussed performing a nipple-sparing mastectomy with the patient"). Thus, instances of the term "discussed" are triggers for ignoring portions of medical text that are associated with the term "discussed." It should be appreciated that a large set of ignore trigger terms and phrases may be identified as indicative of hypotheticals, such as "recommended", "advised", and "planned", and the like, and may be included in the hypothetical dictionary data structure 127.

Similarly, the factual dictionary data structure 128 may include an entry that identifies the term "revealed" as a confirm trigger. That is, in the context of this example, it has been determined that the term "revealed" when used in medical texts, such as a patient's EMR, indicates an actual event, state, or condition of the patient that has occurred (e.g., "Results of the biopsy revealed that the tumor was malignant."). Thus, instances of the term "revealed" are triggers for confirming portions of medical text as being associated with factual statements or factual portions of statements. It should be appreciated that a large set of confirm trigger terms and phrases may be identified as indicative of factual statements or portions of statements, such as "resulted", "results", "the patient has", and the like, and may be included in the factual dictionary data structure 128.

The hypothetical span analyzer 124 uses the hypothetical dictionary data structure 127 and factual dictionary data structure 128 to search the parse tree data structure generated by the parse tree engine 122 to identify instances within the parse tree data structure of tokens associated with nodes that match the ignore triggers or confirm triggers. Both sets of triggers are searched for in the parse tree data structure and corresponding spans of text are then identified based on the parse tree and the matching nodes. The spans are identified as the sub-trees of the nodes matching the particular trigger. Thus, a hypothetical span is the sub-tree portion of the parse tree data structure corresponding to a node matching an ignore trigger. A factual span is the sub-tree portion of the parse tree data structure corresponding to a node matching a confirm trigger. It can be the case that a factual span may be found within a hypothetical span in which case the factual span is removed from the hypothetical span and is considered to be associated with a confirm trigger and thus, directed to a factual portion of text. The operations performed by the hypothetical span analyzer 124 will be described in greater detail hereafter.

The hypothetical span analyzer 124 identifies the hypothetical and factual spans within the parse tree data structure generated by the parse tree engine 122 and provides this information to the medical text annotator 126. The medical text annotator 126 processes the hypothetical spans and creates annotations (metadata) based on the sub-tree of the parsed medical text that denote which portions of the medical text are associated with hypothetical statements, or hypothetical portions of statements, and which portions of the medical text are associated with factual statements, or factual portions of statements. The medical text annotator 126 performs noun-verb disambiguation for trigger terms based on the tuples found in the hypothetical spans and the comparison to their usage in a parse tree pattern. In other words, the output of hypothetical span analyzer 124 is used by medical text annotator 126 to find a way to treat the annotations within hypothetical spans (e.g., ignoring all annotations associated with hypothetical spans, converting annotations associated with hypothetical spans to other annotations, or the like). These annotations may be provided in addition to other annotations generated by other annotators operating on the medical text and may be stored in metadata associated with the medical text. This metadata may be stored as a separate but associated data structure or may be stored as a portion of the data structure housing the medical text content (e.g. as part of the patient EMR data structures). It should be appreciated that once this operation is performed on a portion of a patient's EMR data structure, the operation need not be performed again since the metadata specifically identifies which portions of the EMR data structure are hypothetical and which are not. However, the mechanisms of the illustrative embodiments may operate on the patient EMR again in cases where new content has been added to the patient EMR, modifications to the dictionaries 127-128 are performed, or the like.

The resulting annotated medical text data structures may be provided to the cognitive system 100 for use in performing a cognitive operation on the medical text. In some illustrative embodiments, these cognitive operations utilize the hypothetical/factual annotations to determine how much to weight each portion of the medical text as part of the cognitive operation. For example, in some illustrative embodiments, portions of the medical texts that are associated with hypothetical annotations in the metadata of the medical texts may be essentially ignored by associated a zero weight factor with these portions of the medical text whereas portions of medical text associated with factual annotations are given a predefined weight which may be modified by other weights for other aspects of the medical text depending on the particular implementation. In some illustrative embodiments, the metadata itself may comprise a pruned parse tree representation of the medical text where the pruned parse tree corresponds to the original parse tree but with sub-trees corresponding to hypothetical spans of text having been removed, or pruned, from the parse tree, thereby causing the cognitive system to ignore those portions of the medical text when performing its cognitive operations.

In one illustrative embodiment, the cognitive operation performed by the cognitive system 100 is a medical treatment recommendation cognitive operation which will ignore the portions of medical text associated with hypothetical annotations and base treatment recommendations only on the portions of medical text associated with factual annotations or portions that are specifically not associated with a hypothetical annotation (e.g., other portions of the medical text that are not associated with either a hypothetical annotation or factual annotation and thus, are indeterminate).

It should be appreciated that while both hypothetical and factual dictionary data structures 127-128 are shown in the depicted embodiment, the illustrative embodiments do not require both types of data structures to be present in order to perform their operations. To the contrary, in some illustrative embodiments, only a hypothetical dictionary data structure 127 may be utilized such that any portions of the parse tree that do not match an ignore trigger or are part of a sub-tree associated with a node matching an ignore trigger, set forth in the hypothetical dictionary data structure 127, are considered to be associated with a factual portion of content. Thus, in this embodiment, only a search for ignore triggers is performed with anything else in the parse tree being considered factual.

Thus, the illustrative embodiments provide a mechanism for distinguishing between hypothetical portions of textual statements and factual portions of textual statements. Based on this distinction, appropriate annotations are applied to the portions of textual statements which may then be used to modify the cognitive operations performed based on the text. In particular, hypothetical portions of textual statements may be given relatively less weight or consideration than factual portions of textual statements, and in some cases may be completely ignored when performing the cognitive operations on the text.

As noted above, the present disclosure can provide a specific improvement to the way in which a cognitive system operates. Such cognitive systems are implemented on one or more data processing systems or computing devices. FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present disclosure are located. In one illustrative embodiment, FIG. 2 represents a server computing device, such as a server 104, which implements a cognitive system and a QA system pipeline (such as the cognitive system 100 and the QA system pipeline 108 shown in FIG. 1) augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS). HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft Windows®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212, includes one or more devices used to transmit and receive data. A memory may be, for example, main memory 208, ROM 224, or a cache such as found in NB/MCH 202.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide medical treatment recommendations for patients. However, it should be appreciated that this is only an example implementation and other healthcare operations may be implemented in other embodiments of the healthcare cognitive system 300.

Moreover, it should be appreciated that while FIG. 3 depicts the patient 302 and user 306 as human figures, the interactions with and between these entities may be performed using computing devices, medical equipment, and/or the like, such that entities 302 and 306 may in fact be computing devices (e.g., client computing devices). For example, the interactions 304, 314, 316, and 330 between the patient 302 and the user 306 may be performed orally (e.g., a doctor interviewing a patient) and may involve the use of one or more medical instruments, monitoring devices, or the like, to collect information that may be input to the healthcare cognitive system 300 as patient attributes 318. Interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, a patient 302 presents symptoms 304 of a medical malady or condition to a user 306, such as a healthcare practitioner, technician, or the like. The user 306 may interact with the patient 302 via a question 314 and response 316 exchange where the user gathers more information about the patient 302, the symptoms 304, and the medical malady or condition of the patient 302. It should be appreciated that the questions/responses may in fact also represent the user 306 gathering information from the patient 302 using various medical equipment (e.g., blood pressure monitors, thermometers, wearable health and activity monitoring devices associated with the patient such as a FitBit®, a wearable heart monitor, or any other medical equipment that may monitor one or more medical characteristics of the patient 302). In some cases, such medical equipment may be medical equipment typically used in hospitals or medical centers to monitor vital signs and medical conditions of patients that are present in hospital beds for observation or medical treatment.

In response, the user 302 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302 from which patient EMRs 322 for the patient may be retrieved, demographic information about the patient, the symptoms 304, and other pertinent information obtained from the responses 316 to the questions 314 or information obtained from medical equipment used to monitor or gather data about the condition of the patient 302. Any information about the patient 302 that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a treatment recommendation 328 to the user 306 to assist the user 306 in treating the patient 302 based on their reported symptoms 304 and other information gathered about the patient 302 via the question 314 and response 316 process and/or medical equipment monitoring/data gathering. The healthcare cognitive system 300 operates on the request 308 and patient attributes 318 utilizing information gathered from the medical corpus and other source data 326, treatment guidance data 324, and the patient EMRs 322 associated with the patient 302 to generate one or more treatment recommendation 328. The treatment recommendations 328 may be presented in a ranked ordering with associated supporting evidence, obtained from the patient attributes 318 and data sources 322-326, indicating the reasoning as to why the treatment recommendation 328 is being provided and why it is ranked in the manner that it is ranked.

For example, based on the request 308 and the patient attributes 318, the healthcare cognitive system 300 may operate on the request, such as by using a QA pipeline type processing as described herein, to parse the request 308 and patient attributes 318 to determine what is being requested and the criteria upon which the request is to be generated as identified by the patient attributes 318, and may perform various operations for generating queries that are sent to the data sources 322-326 to retrieve data, generate candidate treatment recommendations (or answers to the input question), and score these candidate treatment recommendations based on supporting evidence found in the data sources 322-326. In the depicted example, the patient EMRs 322 is a patient information repository that collects patient data from a variety of sources (e.g., hospitals, laboratories, physicians' offices, health insurance companies, pharmacies, etc.). The patient EMRs 322 stores various information about individual patients, such as patient 302, in a manner (structured, unstructured, or a mix of structured and unstructured formats) that the information may be retrieved and processed by the healthcare cognitive system 300. This patient information may comprise various demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient 302, the patient's corresponding EMRs 322 from this patient repository may be retrieved by the healthcare cognitive system 300 and searched/processed to generate treatment recommendations 328.

The treatment guidance data 324 provides a knowledge base of medical knowledge that is used to identify potential treatments for a patient based on the patient's attributes 318 and historical information presented in the patient's EMRs 322. This treatment guidance data 324 may be obtained from official treatment guidelines and policies issued by medical authorities (e.g., the American Medical Association), may be obtained from widely accepted physician medical and reference texts (e.g., the Physician's Desk Reference), insurance company guidelines, or the like. The treatment guidance data 324 may be provided in any suitable form that may be ingested by the healthcare cognitive system 300 including both structured and unstructured formats.

In some cases, such treatment guidance data 324 may be provided in the form of rules that indicate the criteria required to be present, and/or required not to be present, for the corresponding treatment to be applicable to a particular patient for treating a particular symptom or medical malady/condition. For example, the treatment guidance data 324 may comprise a treatment recommendation rule that indicates that for a treatment of decitabine, strict criteria for the use of such a treatment is that the patient 302 is less than or equal to 60 years of age, has acute myeloid leukemia (AML), and no evidence of cardiac disease. Thus, for a patient 302 that is 59 years of age, has AML, and does not have any evidence in their patient attributes 318 or patient EMRs indicating evidence of cardiac disease, the following conditions of the treatment rule exist:

Age<=60 years=59 (MET);
Patient has AML=AML (MET); and
Cardiac Disease=false (MET)

Since all of the criteria of the treatment rule are met by the specific information about this patient 302, then the treatment of decitabine is a candidate treatment for consideration for this patient 302. However, if the patient had been 69 years old, the first criterion would not have been met and the Decitabine treatment would not be a candidate treatment for consideration for this patient 302. Various potential treatment recommendations may be evaluated by the healthcare cognitive system 300 based on ingested treatment guidance data 324 to identify subsets of candidate treatments for further consideration by the healthcare cognitive system 300 by scoring such candidate treatments based on evidential data obtained from the patient EMRs 322 and medical corpus and other source data 326.

For example, data mining processes may be employed to mine the data in sources 322 and 326 to identify evidential data supporting and/or refuting the applicability of the candidate treatments to the particular patient 302 as characterized by the patient's patient attributes 318 and EMRs 322. For example, for each of the criteria of the treatment rule, the results of the data mining provide a set of evidence that supports giving the treatment in the cases where the criterion is "MET" and in cases where the criterion is "NOT MET." The healthcare cognitive system 300 processes the evidence in accordance with various cognitive logic algorithms to generate a confidence score for each candidate treatment recommendation indicating a confidence that the corresponding candidate treatment recommendation is valid for the patient 302. The candidate treatment recommendations may then be ranked according to their confidence scores and presented to the user 306 as a ranked listing of treatment recommendations 328. In some cases, only a highest ranked, or final answer, is returned as the treatment recommendation 328. The treatment recommendation 328 may be presented to the user 306 in a manner that the underlying evidence evaluated by the healthcare cognitive system 300 may be accessible, such as via a drilldown interface, so that the user 306 may identify the reasons why the treatment recommendation 328 is being provided by the healthcare cognitive system 300.

In accordance with the illustrative embodiments herein, the healthcare cognitive system 300 is augmented to include a medical text ingestion engine 340, which may be the medical text ingestion engine 120 in FIG. 1, for example. The medical text ingestion engine 340 operates on one or more of the corpora of data 322-326 to ingest those one or more corpora 322-326 to generate an in-memory representation of the medical texts usable by the healthcare cognitive system 300 to perform its cognitive operations. The ingestion operation comprises analysis of the medical texts to identify various features of the medical texts, such as parts of speech of the various terms and phrases used in the medical text, ontological correlations indicating instances of concepts within the medical text, and other annotation of the medical texts to generate metadata annotations that may be used by the healthcare cognitive system 300 to perform its cognitive operations. Other appropriate processing of the corpora 322-326, as is generally known with regard to cognitive system ingestion mechanisms, may also be implemented as part of the ingestion operation.

In accordance with the illustrative embodiments, the medical text ingestion engine 340 is augmented to include logic for performing analysis to distinguish hypothetical portions of text and factual portions of text in the medical texts of the one or more corpora 322-326. In one illustrative embodiment, the medical text ingestion engine 340 analyzes patient EMRs 322 to distinguish and annotate hypothetical portions of text and factual portions of text. The resulting annotated medical texts may then be utilized by the healthcare cognitive system 300 to perform a cognitive operation, such as a medical treatment recommendation, giving appropriate weight to the hypothetical and factual portions of text (e.g., zero weight to the hypothetical portions and more than zero weight to the factual portions of text).

For example, the medical text ingestion engine 340 may retrieve a patient EMR 323 from the patient EMR corpus 322, which may be a patient registry or the like. The textual content of the patient EMR 323 may then be analyzed by the parse tree engine 342 to generate a parse tree data structure representing the textual content. The parse tree data structure comprises nodes representing tokens in the text, where the token is a term or phrase, and edges connecting the nodes representing relationships between the nodes. Moreover, some nodes may represent logical relationships (e.g., AND, OR, ANDNOT, etc.) between portions of the text. Nodes may have associated attributes including parts of speech attributes which may be used to assist the analysis when determining whether a node corresponds to an ignore trigger or confirm trigger, as discussed hereafter.

While FIG. 3 is depicted with an interaction between the patient 302 and a user 306, which may be a healthcare practitioner such as a physician, nurse, physician's assistant, lab technician, or any other healthcare worker, for example, the illustrative embodiments do not require such. Rather, the patient 302 may interact directly with the healthcare cognitive system 300 without having to go through an interaction with the user 306 and the user 306 may interact with the healthcare cognitive system 300 without having to interact with the patient 302. For example, in the first case, the patient 302 may be requesting 308 treatment recommendations 328 from the healthcare cognitive system 300 directly based on the symptoms 304 provided by the patient 302 to the healthcare cognitive system 300. Moreover, the healthcare cognitive system 300 may actually have logic for automatically posing questions 314 to the patient 302 and receiving responses 316 from the patient 302 to assist with data collection for generating treatment recommendations 328. In the latter case, the user 306 may operate based on only information previously gathered and present in the patient EMR 322 by sending a request 308 along with patient attributes 318 and obtaining treatment recommendations in response from the healthcare cognitive system 300. Thus, the depiction in FIG. 3 is only an example and should not be interpreted as requiring the particular interactions depicted when many modifications may be made without departing from the spirit and scope of the present disclosure.

Thus, the illustrative embodiments provide mechanisms for analyzing natural language content of a document, such as a medical text, to identify portions of text that reference hypothetical events, status, conditions, or the like and differentiate these hypotheticals from portions of text referencing actual facts. Corresponding annotations are provided for the various portions of text to identify them as hypothetical or factual based on the results of such analysis and these annotations are then provided to a cognitive system for use when performing its cognitive operations.

As noted above, in some illustrative embodiments, these cognitive operations may comprise a machine learning model performing machine learning, such as machine learning for determining appropriate medical treatment recommendations. For example, as part of a machine learning operation performed by a machine learning model, the patient EMRs for a plurality of patients may be retrieved from a patient registry of a corpus and used to draw correlations between patient attributes and corresponding prescribed treatments. For example, various medical maladies, patient attributes (e.g., age, gender, height, weight, particular lab results, etc.), and their corresponding treatments prescribed by medical personnel may be identified in the patient EMRs and used to generate a machine learning model of medical treatment recommendations. Such machine learning may correlate these medical maladies, patient attributes, and prescribed treatments, identify other corroborating evidence in the corpus or corpora, including other medical texts such as guidelines, positional papers, and the like, and generate a confidence in the treatment recommendation correlation.

Figure 4:
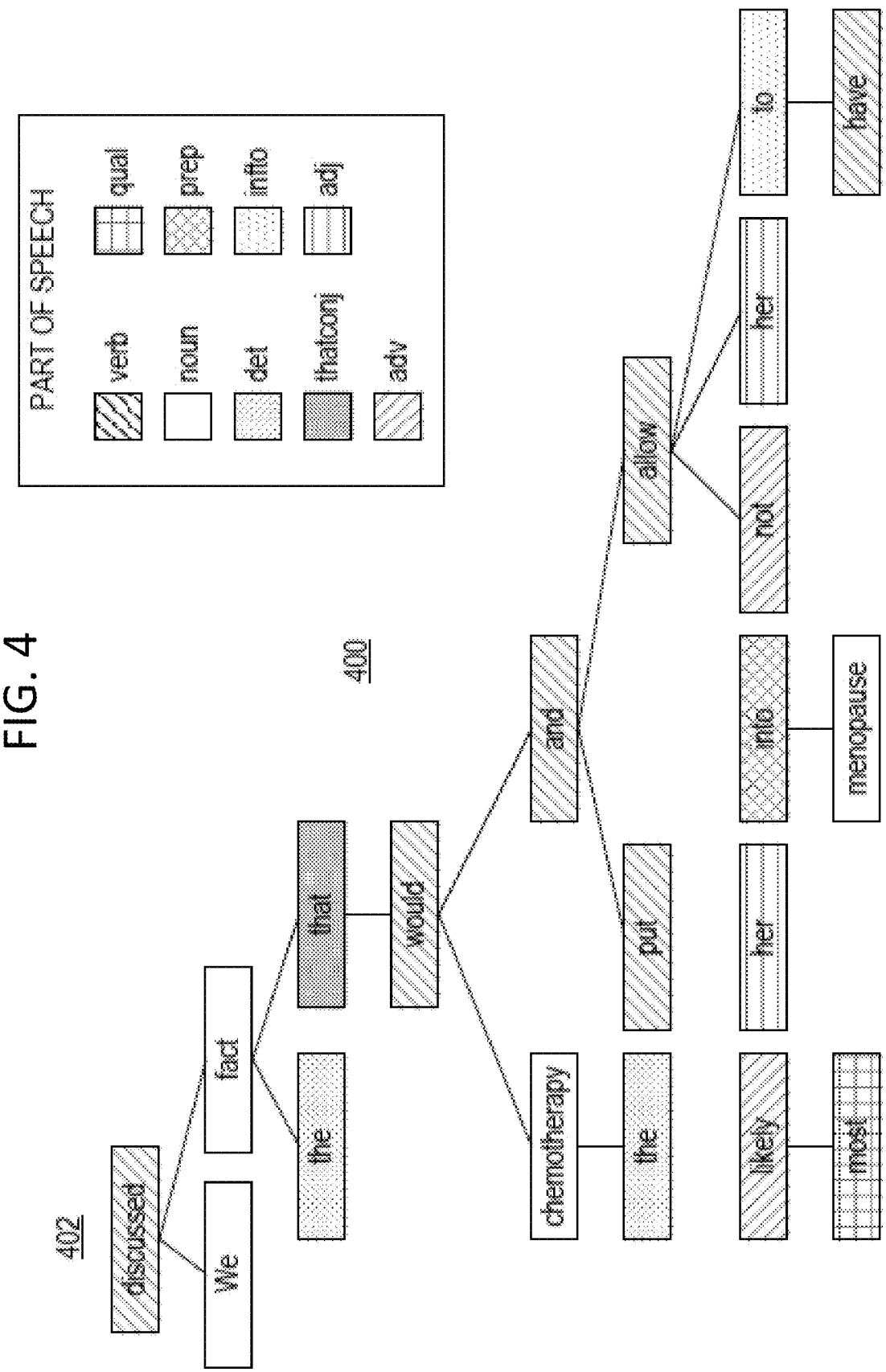
FIG. 4 is an example parse tree data structure representation of an example note, composed by a medical professional, which may be part of a patient's electronic medical record (EMR), in accordance with one illustrative embodiment.

For example, FIG. 4 is an example parse tree data structure representation of an example note, composed by a medical professional, which may be part of a patient's EMR. In the depicted example, the parse tree is for the statement, "We discussed the fact that the chemotherapy would most likely put her into menopause and not allow her to have more children."

The parse tree data structure is provided to the hypothetical span analyzer 344 which analyzes each of the nodes of the parse tree data structure to identify nodes matching ignore triggers specified by the hypothetical dictionary data structures 347 and confirm triggers specified by the factual dictionary data structures 348. The hypothetical span analyzer 344, for example, may receive a parse tree data structure for each sentence of the medical text, or depending on the particular implementation, a parse tree for any size portion of text from the medical text retrieved by the medical text ingestion engine 340. For each node in the parse tree data structure, a determination is made as to whether the node's token corresponds to an ignore trigger specified in the hypothetical dictionary data structures 347. If so, the part of speech attribute of the node is compared to a part of speech attribute of the ignore trigger to determine if there is a match in the part of speech with this match being a verb part of speech. If the part of speech attribute of the node is a verb and the node's parent node's part of speech is a verb, then the sub-tree of the node is selected to be an ignore sub-tree with the node's parent node being the root of that ignore sub-tree.

The check for part of speech tag of the parent node is performed in order to determine if the sentence is passive or active, such as a sentence containing "was recommended" indicates a passive sentence. If the trigger is "recommended" and "recommended" is identified as a verb by the parse tree as well as its parent node being "was", the hypothetical subtree starts from "was" instead of "recommended." This is to capture phrases such as "were discussed" where "discussed" is the identified node and "were" is a parent node of the identified node, for example. If the node and the parent node are not both verbs, then the sub-tree of the node is selected with that node being the root of the ignore sub-tree.

The reason that verbs are targeted for this process is that some terms or phrases may be used as multiple parts of speech (e.g., both a noun and a verb). However, in some implementations, hypothetical trigger terms or phrases are more often used as verbs and thus, the identification of a trigger term that is a verb is likely to indicate a hypothetical span of text. It should be appreciated that other implementations may make more complex analysis of the parts of speech and may not be dependent upon whether or not the parts of speech of the node token and the ignore trigger are verbs.

For each node of the ignore sub-tree, a determination is made as to whether the node corresponds to a confirm trigger. If a node of the ignore sub-tree matches a confirm trigger, then the sub-tree of that node is selected and that confirm sub-tree is removed from the ignore sub-tree. The resulting ignore sub-tree with any confirm sub-trees removed, is returned for annotation with an ignore annotation, or hypothetical annotation, while the confirm sub-trees are returned for confirm, or factual, annotations. Trees or sub-trees of the parse tree data structure that do not correspond to an ignore sub-tree may also be annotated with a confirm annotation, or factual annotation, or may otherwise not be annotated with regard to confirm/ignore annotations, depending on the particular implementation.

If it is determined that the part of speech of the token of the node matching an ignore trigger is a noun and not a verb, additional analysis of other natural language resources corresponding to the token of the node may be analyzed to generate a confidence score as to whether or not the token of the node is likely indicative of a hypothetical. For example, definition information from a dictionary data structure indicating the part of speech of the various uses of the token and the tense information for the various uses, n-grams, and the like may be analyzed to generate a score of the likelihood of the token being indicative of a hypothetical span of text and thus, matching the ignore trigger. This analysis is performed since the same token may represent both an ignore trigger and a confirm trigger depending on the way in which the token is utilized in the text. As an example, consider the term "considering" in the following sentences:

(1) "The patient has been strongly considering a prophylactic mastectomy on the right breast for ultimate risk reduction."

(2) "The patient has been advised considering the prophylactic mastectomy on the right breast for ultimate risk reduction."

In sentence 1 above, the term "considering" is an ignore trigger as it is describing a hypothetical future possibility of the patient undergoing a prophylactic mastectomy. In sentence 2 above, the term "considering" is a confirm trigger as the term is referring to an actual event that occurred (i.e. the medical professional advising the patient about the prophylactic mastectomy). In sentence 2, noun-verb disambiguation is performed based on the part of speech and tense information associated with the tokens and part of speech and tense information in the dictionary to determine whether the instance of the token "considering" is an ignore trigger or confirm trigger.

The n-grams used to disambiguate these two sentences will be different: <noun> <adverb> considering <noun-procedure> and <noun> <verb> considering <noun-procedure>. Because the first sentence matches the tuples in a training set, sentence 1 will be identified as hypothetical whereas sentence 2 will not.

Returning to FIG. 4, the sentence corresponding to the parse tree 400 shown in FIG. 4 illustrates a simple example of a sentence with an ignore trigger and corresponding ignore sub-tree that does not comprise an embedded confirm sub-tree. As shown in FIG. 4, the node 402 having token "discussed" is matched to a corresponding ignore trigger in the hypothetical dictionary data structures 347. Taking this node 402 as a root node of an ignore sub-tree comprising the child nodes of the node 402, the hypothetical span analyzer 344 searches the ignore subtree for any confirm trigger matches that are a sibling or child of the "discussed" node 402 but there are none in this example. As a result, the whole tree 400 rooted with the "discussed" node 402 is selected as an ignore sub-tree and flagged for annotation with an ignore or hypothetical annotation by the medical text annotator 346.

The annotated ignore sub-tree 400 may then be processed by the healthcare cognitive system 300 to perform a cognitive operation with appropriate weighting given to the ignore sub-tree 400. In some illustrative embodiments, this weighting involves ignoring the ignore sub-tree 400 when performing the corresponding cognitive operation. In some illustrative embodiments, this cognitive operation is a machine learning operation performed by a machine learning model of the healthcare cognitive system used with regard to medical treatment recommendations. In some illustrative embodiments, this cognitive operation is the operation of providing the medical treatment recommendation to a user request (such as the user request 308 in FIG. 3). In other illustrative embodiments, other cognitive operations that may be affected by the validity, trust, or confidence attributed to hypothetical spans of text, may operate based on the hypothetical (or ignore) annotations and factual (or confirm) annotations generated by the mechanisms of the illustrative embodiments.

Figure 5:
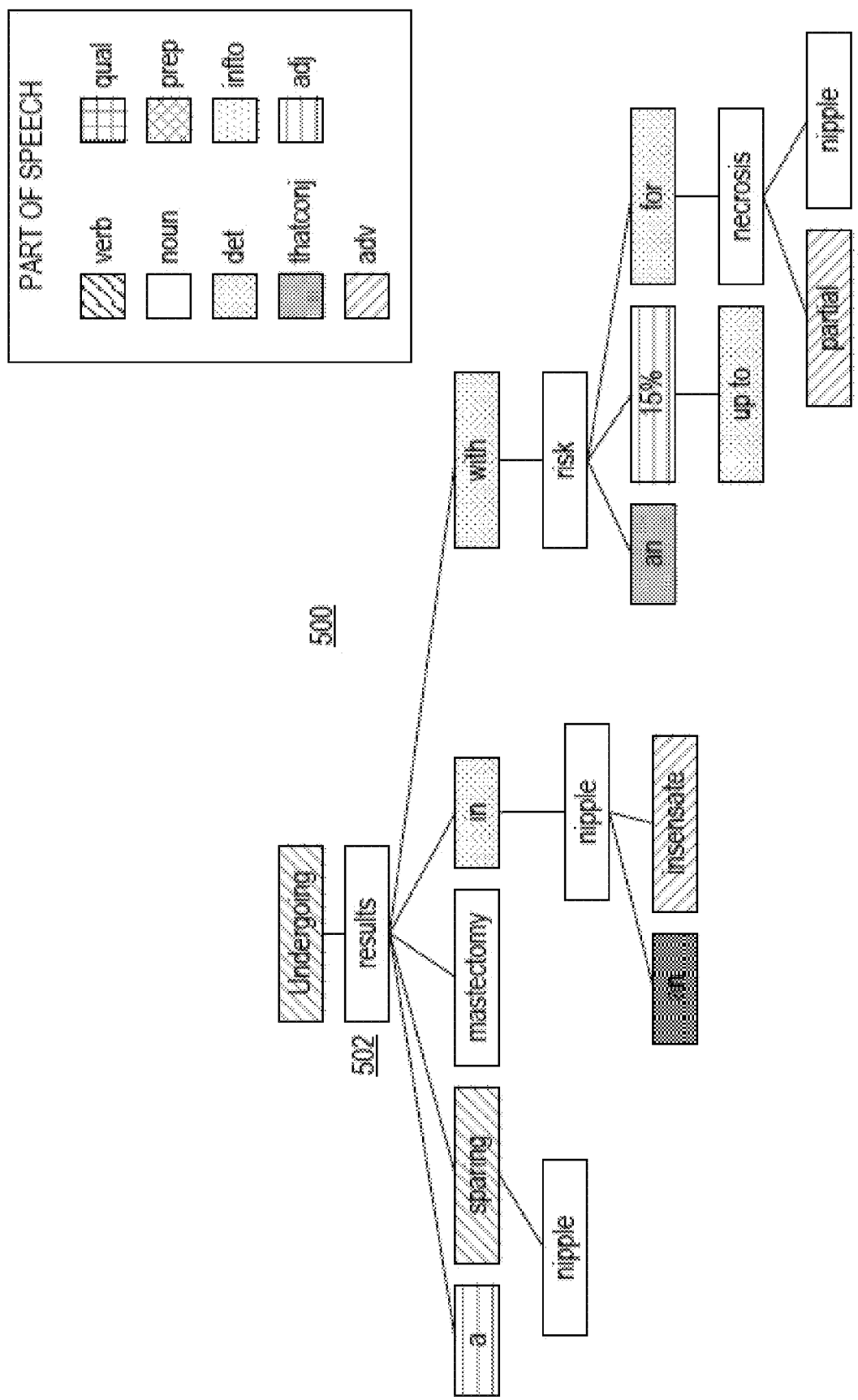
FIG. 5 is an example of another parse tree data structure for a sentence in which disambiguation of the node corresponding to an ignore trigger is performed in accordance with one illustrative embodiment.

FIG. 5 is an example of another parse tree data structure for a sentence in which disambiguation of the node corresponding to an ignore trigger is performed in accordance with one illustrative embodiment. As shown in FIG. 5, the parse tree 500 corresponds to the statement, "Undergoing a nipple-sparing mastectomy results in an insensate nipple with an up to 15% risk of partial nipple necrosis." When one views the parse tree 500 of this sentence, it can be seen that the term "results in" is a phrase that captures all the tokens that are potentially a hypothetical span, and this is generalizable enough not to cause any wrong annotations in other cases.

Comparing each token of each node in the parse tree 500 to ignore triggers in the hypothetical dictionary data structures 347, the node 502 is correctly identified as matching an ignore trigger but the token is associated with the "noun" part of speech in this example. Therefore, disambiguation of the token corresponding to node 502 is performed based on dictionary information, tense information, n-grams, ontological information, and the like. The disambiguation attempts to match the features of the token of the node 502 to other parts of the sentence (i.e. other parts of the sub-tree of the node 502 to disambiguate the language use of the token). For example, the definition of the term(s) of the token may be compared with other portions of the sentence to determine if it matches the other parts of speech of the other portions of the sentence.

For example, taking the sub-tree of the node 502 the corresponding sentence is, "A nipple-sparing mastectomy results in an insensate nipple." The corresponding dataset of tuples, or n-grams, with a corresponding tuple containing medical adjusted ontology illustrating the part of speech pattern of the above sentence is as follows:

<noun><verb><noun> (this is a straight sentence parse tuple)

where the medical adjusted ontology tuple is:

<noun-procedure><verb><noun-body-part> (this is the sentence parse tuple adjusted for the domain)

The tuples are obtained from the training set. The <noun-procedure> in the above tuple matches "nipple-sparing mastectomy" in the sentence, the <noun-body-part> matches "insensate nipple", and from the dataset of tuples, it is expected that the trigger is a verb not a noun (as XSG identifies it). Because the sentence matches the tuple, it is concluded that the trigger must indeed be a verb and not a noun, and it can be identified as a hypothetical statement.

The dictionary definition of the term "results" that may be utilized in this example to disambiguation the token of node 502 is as follows:

(1) To spring, arise, or proceed as a consequence of actions, circumstances, premises, etc.; be the outcome.

(2) To terminate or end in a specified manner or thing.

From analyzing this information, it can be determined that token "results" of node 502 is being used as a verb in the sentence and thus, is likely an ignore trigger referencing a hypothetical span of text. Hence, the sub-tree of node 502 will be identified as an ignore sub-tree and may be further analyzed with regard to confirm triggers as discussed above. That is, once the part of speech is identified, the definition is parsed for terms. Based on the set of sentence pattern matches, the definition can help to confirm that the "trigger" is indeed correct. For this example, one of the sentence patterns includes "noun-outcomes or calculations". The definition of "result," includes the term "outcome". A set of these patterns that has been denoted by a subject matter expert will help to confirm usage of terms that can be various parts of speech.

As another example, consider the sentence "A mastectomy performed had good results." The corresponding tuple or n-gram for this sentence is as follows:

<noun><verb><adjective><noun> where the medical adjusted ontology tuple is:

<noun-procedure><verb-action-past-tense><noun-outcome/calculation>

The result of analyzing this tuple, dictionary definition, ontology information, etc., indicates that the use of the term "result" is a noun, making it not an ignore trigger match since it is not a verb. If this tuple is not used, the term "results" could be taken as an ignore trigger when it is actually a fact in this sentence. In this particular sentence the matching tuple is noun: mastectomy, verb: performed, verb-action-past-tense: had, and noun-outcome/calculation: good results. It is known from training set data that this tuple is associated with facts and not hypotheticals. Therefore, finding this sentence matches the tuple, the mechanisms of the illustrative embodiment identifies the term "results" as a confirm trigger rather than an ignore trigger.

In order to identify whether a sentence matches a particular tuple, in some illustrative embodiments, the mechanisms of the illustrative embodiments may score the tuples relative to the sentence. For each tuple pattern there is a maximum score for matching the tuple pattern such that when all parts of speech are found within the hypothetical span or the natural language content that contains a hypothetical span the maximum score is associated for the tuple. Each matching item is given a weight in the pattern, with noun and verb having the highest weight and the subject having the next highest weight. The score for the tuple pattern is an aggregate of the weighted value for each matching portion of the tuple pattern and when this the score is higher than a threshold, it can be determined that the tuple pattern has been sufficiently matched, and the term should be treated as a trigger (e.g., a hypothetical or confirm trigger depending on whether the tuple is for confirm or hypothetical trigger identification).

For example, in the above tuple pattern, the weights for the various parts of speech may be as follows: <noun> (2) <verb> (6) <adjective> (1) <noun-procedure> (3), <verb-action past tense> (2) <noun-outcome/calculation> (4), which gives a maximum score of 18. A threshold for confirming a trigger is highly weighted towards the correct parts of speech and thus, an example threshold score could be determined to be 10 such that if a portion of text matches parts of the tuple pattern so as to generate a weighted score of 10 or greater, it is considered to be a trigger. If more than one of these tuple patterns are matched over their corresponding threshold values, then confirmation of the trigger can be performed based on the number of matches.

It should be appreciated that the above process for identifying ignore sub-trees and confirm sub-trees may be performed with regard to each portion of text within the medical text (e.g., each sentence) such that the entirety of the medical text is analyzed to identify ignore (hypothetical) sub-trees and confirm (factual) sub-trees. The ignore sub-trees represent the hypothetical spans while the confirm sub-trees represent the factual spans. These hypothetical spans and factual spans may be provided to a medical text annotator (such as the medical text annotator 346 in FIG. 3) which generates the corresponding ignore (hypothetical) annotations and confirm (factual) annotations in the metadata 325 of the medical text (e.g., EMR 323) pointing to the corresponding hypothetical spans and factual spans in the medical text. The medical text (e.g., EMR 323) and the metadata 325 are returned to the healthcare cognitive system 300 for use in performing cognitive operations.

In some illustrative embodiments, the identification of hypothetical spans of text and annotation of such hypothetical spans of text, which corresponds to the ignore sub-trees identified by the mechanisms of the illustrative embodiments, may be used to ignore the hypothetical spans when performing the machine learning operations to learn the correlations of medical malady, patient attributes, and treatment. Thus, when the machine learning operation encounters a portion of text that is annotated as being a hypothetical span of text, that portion of text is ignored and not processed as part of the machine learning operation. In some illustrative embodiments, it may be determined that, while hypothetical in nature, the hypothetical span of text may still provide some insight into the validity of correlations of medical malady, patient attributes, and treatment and may instead of ignoring these portions of text, may give them relatively smaller weight during the evaluation than other portions of text that are determined to be associated with factual content. Thus, for example, when identifying evidential support for a correlation, hypothetical spans of text will provide relatively smaller amounts of evidential support for/against the correlation than other portions of text identified as being factual in nature.

Similarly, the cognitive operation may comprise the actual runtime determination of a treatment recommendation for a particular identified patient, such as described in the context of FIG. 3 above. In such a case, similar considerations of hypothetical spans of text may be performed by the healthcare cognitive system 300 when generating a treatment recommendation 328 to be returned to the user 306. That is, the hypothetical spans of text may be ignored or given relatively smaller weight, depending on the particular implementation, when evaluating the patient EMRs to determine appropriate treatments based on other evidential information in the corpora 322-326.

Hence, mechanisms are provided, in a data processing system having a processor and at least one memory, where the at least one memory has instructions which are executed by the processor and configure the processor to perform the operations corresponding to one or more of the illustrative embodiments described above. In one illustrative embodiment, these operations include: (1) receiving, by the data processing system, natural language content; (2) analyzing, by the data processing system, the natural language content to generate a parse tree, wherein the parse tree is a hierarchical representation of the natural language content comprising nodes corresponding to terms or phrases in the natural language content and edges linking the nodes; (3) processing, by the data processing system, the parse tree data structure to identify one or more instances of hypothetical triggers in the natural language content, wherein hypothetical triggers are terms or phrases indicative of a hypothetical statement; and (4) performing, by the data processing system, a cognitive operation based on the natural language content, wherein the cognitive operation is performed with portions of the natural language content corresponding to the one or more identified instances of hypothetical triggers being given relatively lower weight than other portions of the natural language content.

In some illustrative embodiments, these operations further include removing, by the data processing system, one or more sub-tree data structures of the parse tree data structure that correspond to the one or more instances of hypothetical triggers, to thereby generate a hypothetical pruned parse tree data structure, wherein the cognitive operation is performed based on the hypothetical pruned parse tree data structure. In still other illustrative embodiments, performing the cognitive operation includes training, by the data processing system, a model of a natural language processing (NLP) system based on the identification of the one or more instances of hypothetical triggers in the natural language content, and performing, by the NLP system, natural language processing of natural language content based on the trained model.

In still further illustrative embodiments, processing the parse tree data structure further includes, for each instance of a hypothetical trigger found in the parse tree data structure: analyzing the hypothetical trigger using a dictionary data structure to determine a part-of-speech attribute of the hypothetical trigger; and utilizing the determined part-of-speech attribute to determine a measure of whether or not the hypothetical trigger corresponds to a hypothetical statement. Moreover, utilizing the determined part of speech attribute to determine a measure of whether or not the hypothetical trigger corresponds to a hypothetical statement may include: generating a tuple representation of a sub-tree data structure corresponding to the hypothetical trigger; retrieving, from the dictionary data structure, one or more dictionary definitions of a term present in the hypothetical trigger; and determining a part-of-speech attribute of the hypothetical trigger based on a correlation of the tuple representation of the sub-tree data structure with the one or more dictionary definitions. In response to the part-of-speech attribute indicating that the hypothetical trigger is a noun, then the sub-tree data structure corresponding to the hypothetical trigger is determined to not be directed to a hypothetical statement.

In yet other illustrative embodiments, the NLP system is a medical treatment recommendation system, and the cognitive operation includes generating treatment recommendations based on content of a patient electronic medical record. Moreover, the data processing system may be a backend data processing system of the medical treatment recommendation system.

In some illustrative embodiments, processing the parse tree data structure further includes processing the parse tree data structure to identify instances of factual triggers, wherein factual triggers are terms or phrases indicative of a factual statement. Also, the operation may include determining if a factual sub-tree is present within a hypothetical sub-tree and removing the factual sub-tree from the hypothetical sub-tree to generate a modified hypothetical sub-tree prior to further processing of the modified hypothetical sub-tree.

Figure 6A:
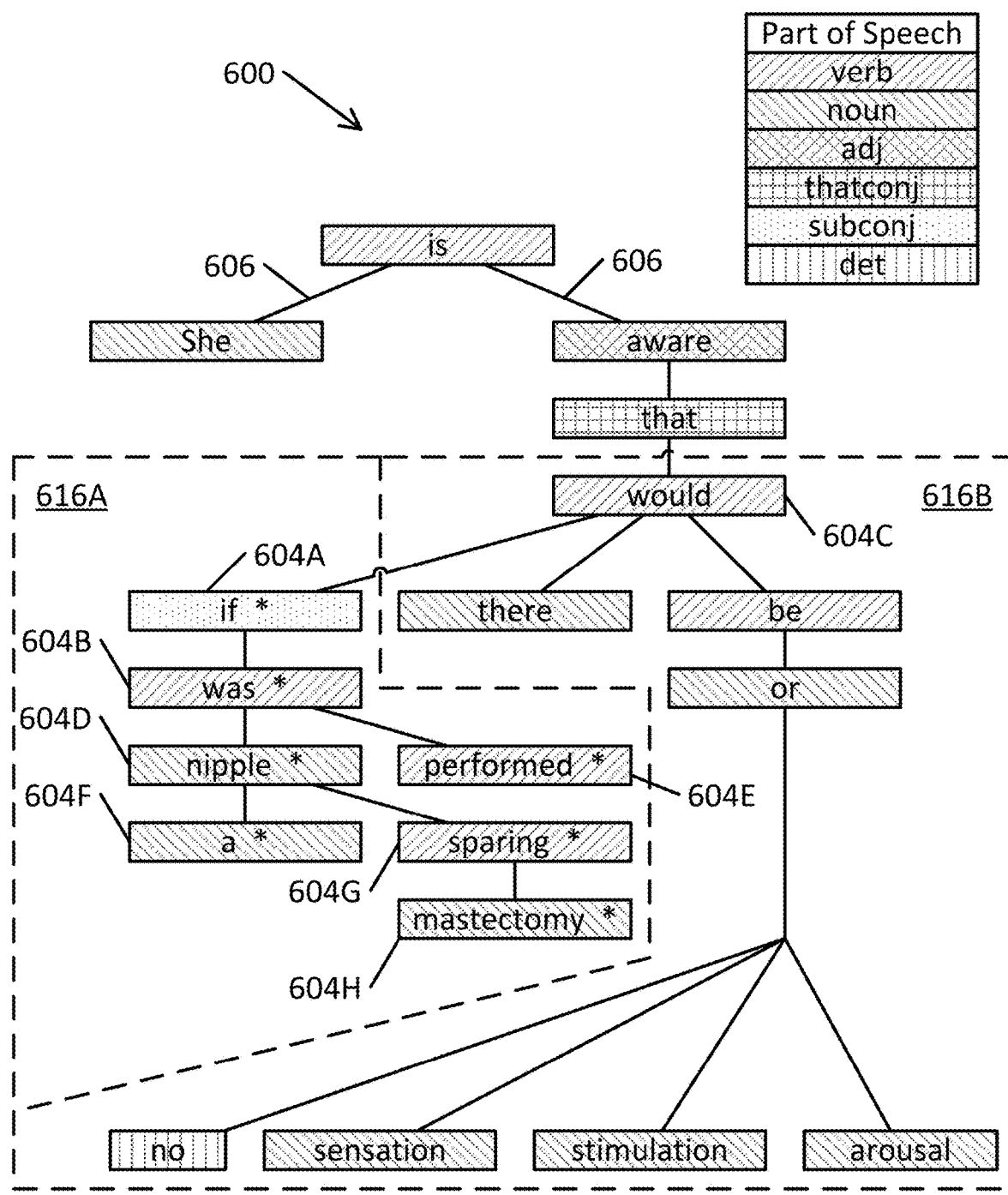
FIG. 6A is an example of another parse tree data structure for a sentence describing the nodes and connecting edges of the sentence in accordance with an illustrative embodiment.
Figure 6B:
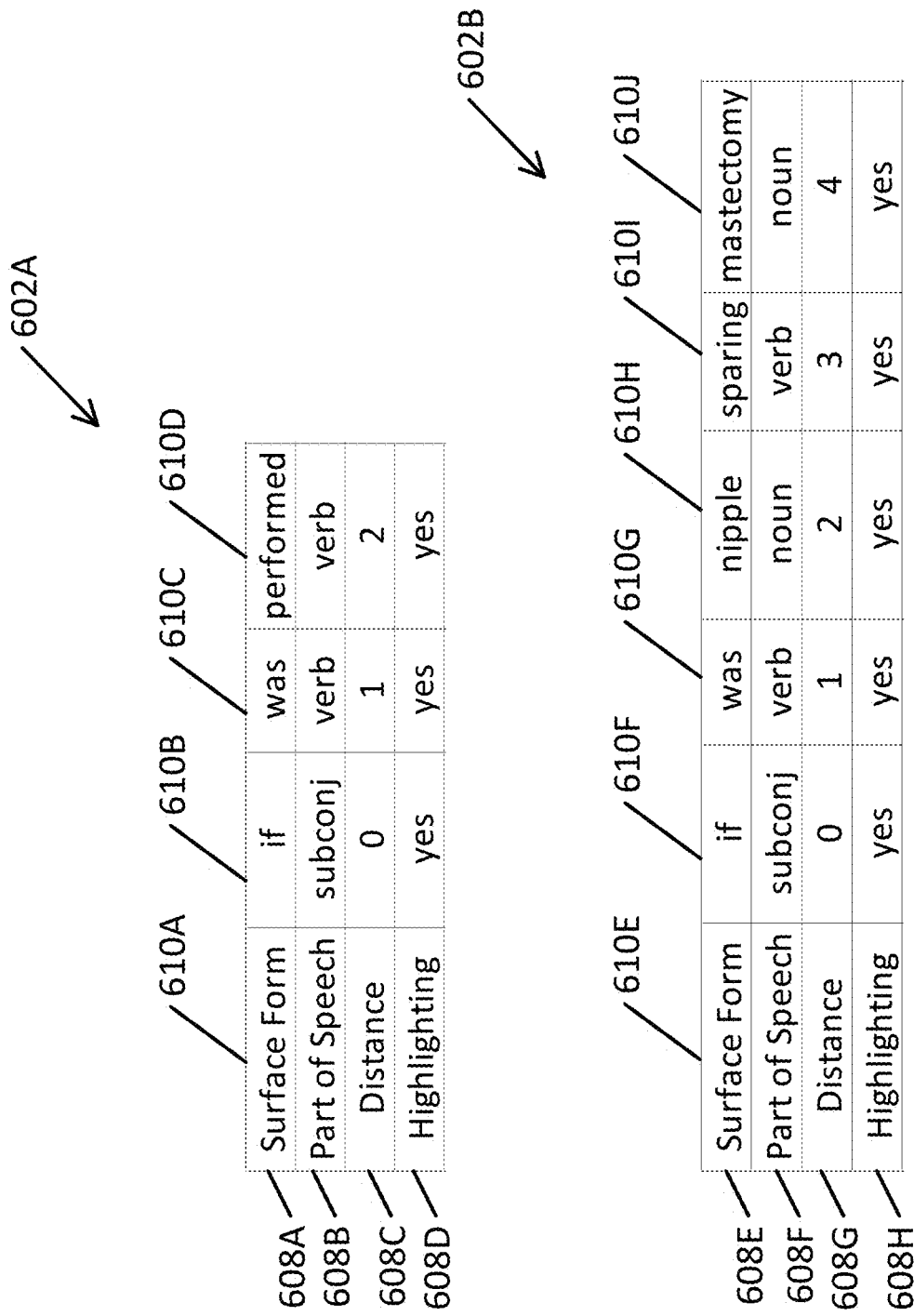
FIG. 6B is an example of two tables of the parse tree along two traversals.
Figure 6C:
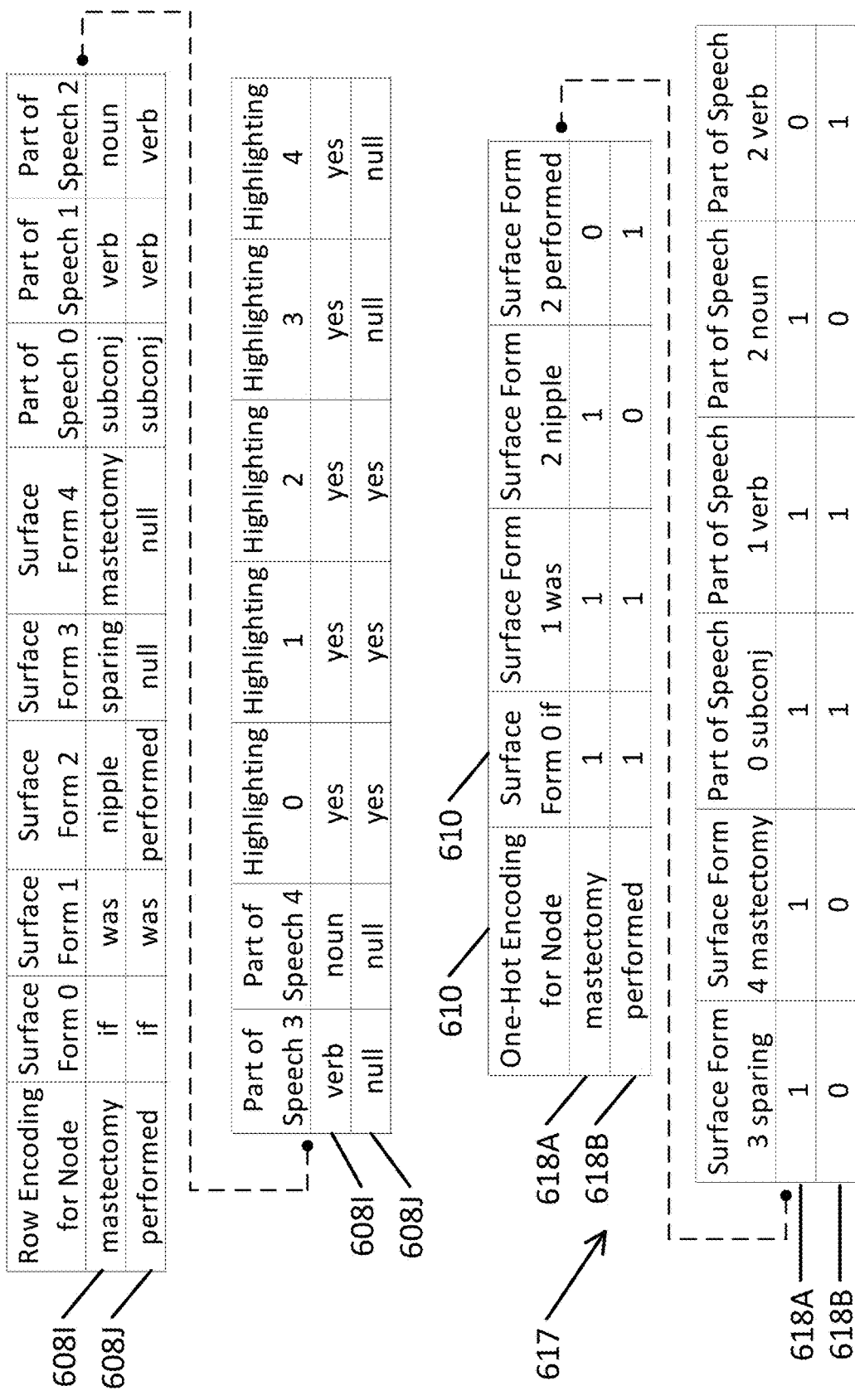
FIG. 6C is an example comparison table of two traversals in tabular form and their corresponding one-hot encoded vectors.

FIG. 6A is an example of another parse tree data structure 600 for a sentence describing the nodes 604 and connecting edges 606 of the sentence in accordance with an illustrative embodiment. FIG. 6B is an example of tables 602 of parse tree 600 along two traversals. FIG. 6C is an example of comparison table 614 of two traversals and their corresponding one-hot encoded vectors in vector table 617 (although only a portion of table 617 is visible). FIGS. 6A-6C are based on the sentence, "She is aware that if a nipple sparing mastectomy was performed, there would be no sensation, stimulation, or arousal." In this sentence, there are two hypothetical triggers, with one being "if" and the other being "would be". FIGS. 6A-6C will now be discussed together.

In the illustrative embodiment, parse tree 600 includes many nodes 604 such as if node 604A, was node 604B, would node 604C, nipple node 604D, performed node 604E, a node 604F, sparing node 604G, and mastectomy node 604H. While all of nodes 604 are connected by edges 606, some nodes 604 are directly connected to other nodes 604 that are adjacent thereto (see FIG. 6A).

Each table 602 includes rows 608 and columns 610, wherein rows 608 contain attributes of nodes 604. Each table 602 represents a traversal, which is a pathway from a trigger node (such as if node 604A) to a target node. In the illustrative embodiment, table 602A represents the traversal from if node 604A to performed node 604E, and table 602B represents the traversal from if node 604A to mastectomy node 604H. In the illustrative embodiment of tables 602A and 602B, rows 608B and 608F include the "Part of Speech", rows 608C and 608G include the "Distance", and rows 608D and 608H include "Highlighting". In other embodiments, table 602 can include other attributes of nodes 604, such as "slot name" (the label associated with an edge 606 between two nodes 604, e.g., "vadj", "obj", "top", "subj", etc.), "horizontal" (the horizontal direction(s) of emanating edges 606, e.g., right and left), and "vertical" (the vertical direction(s) of emanating edges 606, e.g., up and down).

In the illustrative embodiment, rows 608C and 608G refer to the distance from the trigger that the target is. For example, in table 602B, the trigger is if node 604A and a distance of "4" can be calculated to mastectomy node 604H. However, in some embodiments, the distance is broken into bins having a predetermined or configurable width or widths. For example, if a bin were two positions wide, then the value for node 604H would be "2", and if a bin were four positions wide, then the value for node 604H would be "1". Such a feature can be used in recognition that different sentences may have effectively similar nodes, but the nodes may be different distances from the trigger. In some embodiments, every non-distance attribute includes its respective distance to distinguish what stage of the traversal it appears in. For example, if this practice were used for making tree table 602A, then row 608B would be: "Part of Speech; subconj_0; verb_1; verb_2".

Tree table 602A represents a traversal from trigger node 604A to target node 604E, so columns 610B-610D are arranged in that order. Similarly, tree table 602B represents a traversal from trigger node 604A to target node 604H, so columns 610F-610J are arranged in that order. In addition, tree tables 602 can be transformed into consideration table 614. More specifically, consideration table 614 can be created by laying out the values of each traversal into a single row. More specifically, rows 608A-608D of tree table 602A are adjacent to one another in row 608I, and rows 608E-608H of tree table 602B are adjacent to one another in row 608J.

In the illustrative embodiment, vector table 617 includes vectors 618A and 618B. Vector 618A is the result of one-hot encoding of row 608I in consideration table 614, and vector 618B is the result of one-hot encoding of row 608J in consideration table 614. Vector table 617 has been constructed as though the traversals that produced rows 608I and 608J are the only traversals present in the training data set. Thereby, the columns 610 represent every unique value present in consideration table 614 (i.e., every combination of an attribute type and the attribute value is represented, although not all of the columns 610 are visible in FIG. 6C). In doing so, the attribute values from consideration table 614 can be transformed into "1's" and "0's" (e.g., the "mastectomy" vector is [1 1 1 0 1 1 1 1 0 . . . ] and the "performed" vector is [1 1 0 1 0 0 1 1 0 1 . . . ]). In some embodiments, there isn't a vector table 617 as shown in FIG. 6C, instead there are a collection of separate vectors and a separate map of what attribute type/value combination is in which position.

In the illustrative embodiment, rows 608E and 608J refer to whether the corresponding node 604 is highlighted or marked. For the sake of simplicity, the "highlighted" nodes 604 in FIG. 6A have been marked with asterisks (*). The highlighting of certain nodes 604 in parse tree 600 has been performed by a third party (such as by humans or other machines/algorithms) to mark hypothetical span 616A in parse tree 600. As will be explained below, this is done for machine learning and training purposes. While parse tree 600 also includes another hypothetical span 616B, only span 616A has been highlighted because highlighting both spans 616A and 616B would not allow parse tree 600 to be used for training. This is because each node 604 is in or out of a span 616 due to its grammatical relationship to a single trigger. When a series of text includes two triggers, the nodes in-span with one trigger will not be in-span with the other trigger, and vice versa. Instead, if it was beneficial to use span 616B for training, then another parse tree (not shown) could be made with only span 616B being highlighted.

The features of parse tree 600, tables 602, consideration table 614, and vectors 618A and 618B allow for structured query language (SQL) operations to be performed on parse tree 600. Thus, an inference algorithm that executes the machine learned model can recognize the occurrence of attribute type/value combinations from the traversals encoded in the training set. Then, the optimal label can be chosen based on the combinations the NLP system has reviewed.

While there are only two tree tables 602 shown in FIG. 6B and only two corresponding consideration tables 614 and vectors 618 shown in FIG. 6C, a full analysis of parse tree can contain more tables and vectors. A consideration table 602 can be made for each possible traversal between any trigger and any target in parse tree 600. Thereby, a vector 618 can be made for each possible traversal between any trigger and any target in parse tree 600 as well.

FIG. 7 is a flowchart of method 700 of finding a span of a parse tree, for example, using one of parse tree data structures 400, 500, and 600 of FIGS. 4, 5, and 6A, respectively. Method 700 starts at polygon 702. At polygon 704, a trigger (for example, a hypothetical trigger) in the parse tree is identified as a starting point, and a tree table is started with the trigger node as the second column (alongside the row labels), with the column being populated by the attributes of the trigger node. At polygon 706, each edge emanating from the previous nodes (in the first iteration, this will be the trigger node) is traversed to the next adjacent nodes (which are now the "target nodes"). At polygon 708, each target node has its attributes entered as a column into its own tree table adjacent to the previous node.

At polygon 710, each tree table is transformed into a single row in a consideration table (for example, as described previously with respect to FIG. 6C). In some embodiments, multiple tree tables can be transformed into a single consideration table at polygon 710, for example, by converting each tree table into a single row, and stacking the rows in the consideration table. The tree tables can be from multiple parallel nodes (i.e., nodes with the same distances from the trigger), such as the "that", "chemotherapy", and "and" nodes in FIG. 4 or the "was" and "would" nodes in FIG. 6A. Alternatively, the tree tables can be from multiple serial nodes (i.e., nodes along a single traversal from the trigger), such as the "and", "allow", and "her" nodes in FIG. 4 or the "was" and "performed" nodes in FIG. 6A.

Method 700 continues at polygon 714, wherein the availability of more previously unvisited nodes (e.g., untabulated nodes) that are connected to the previous node is determined. If there are more nodes to tabulate that haven't already been tabulated, then the corresponding edges are traversed, and those untabulated nodes become the new target nodes. Then polygons 706-714 are repeated until all of the new target nodes (i.e., untabulated nodes that are connected to the trigger) have been tabulated and there are no more nodes left to tabulate. The order by which the parse tree is traversed from the trigger can be determined, for example, by a breadth-first search or a depth-first search.

Once the node tabulations have been completed, method 700 continues at polygon 718, the parse tree analyzes whether there are more triggers in the parse tree. If there are one or more remaining triggers (for example, another hypothetical trigger), then method 700 returns to polygon 704 to make a new span. If not, then method 700 ends at polygon 720.

The features of method 700 allow for the parse tree of a sentence or phrase to be systematically analyzed to find a span of nodes for a given trigger, for example, by a module or modules in medical text ingestion engine 120 (shown in FIG. 1). This capability can be used in many different ways. For example, a clinical trial in search of participants can use an NLP processor to select candidates by evaluating their medical history with the ability to separate factual information from hypothetical subjects therein. For another example, the speed and accuracy with which an NLP processor can answer a natural language question can be increased if the NLP processor is more equipped to separate factual information from hypothetical subjects in the question. For another example, an NLP processor can analyze sentences and mark the triggers and spans therein for use as training material for other learning machines, such as an NLP processor. For another example, a social network of connected individuals can be analyzed to find attributes that satisfy certain criteria, for example, which of a user's connections are close familial relatives (e.g., sharing a common ancestor within two generations of the user). In such an embodiment, the method of analysis may include a check to see if the node (e.g., a person) has already been analyzed as to avoid a loop of analyzing the same nodes repeatedly. In addition, in such an embodiment, the method of analysis may include a search depth limit to stop the search from continuing after a certain number of jumps from the user's direct connections. This may be because the likelihood that another user is a close familial relative significantly diminishes the longer that the chain of connections is.

FIG. 8 is a flowchart of method 800 of using a parse tree to train a natural language processing (NLP) system, for example, to operate on natural language text. Method 800 can be implemented using, for example, server 104 and/or medical text ingestion engine 120 (shown in FIG. 1, albeit with a span analyzer that is different from hypothetical span analyzer 124 discussed above). In the illustrated embodiment, method 800 starts at polygon 802, and at polygon 804, an NLP training machine imports training texts, some of which are highlighted and some of which are non-highlighted, and converts them into training parse trees. At polygon 806, the training consideration tables are made from the training parse trees, for example, by performing method 700 on the training parse trees. In some embodiments, when processing the non-highlighted training parse trees, the tree tables are made from every possible traversal in the parse tree such that every node-target pair has a tree table. This is because the trigger nodes have not been previously identified in the non-highlighted parse trees, although the highlighted parse trees may be treated the same despite their marked trigger nodes. In such embodiments, the training consideration tables also represent every node-target pair.

In the illustrated embodiment, at polygon 808, the training consideration tables are used to train a one-hot encoder. Once this training is complete, at polygon 810, all of the training consideration tables are one-hot encoded. At polygon 812, a projection model (e.g., a deep learning space, such as a nearest neighbor feature space) is generated by analyzing the training one-hot encoded vectors, for example, using principal component analysis (PCA), generalized Hebbian algorithm, and/or various deep learning (i.e., neural net) techniques such as autoencoding and/or embeddings. Once this training is complete, at polygon 814, the training one-hot encoded vectors are processed using the projection model. More specifically, only the processed training vectors that originated from the highlighted parse trees are projected at polygon 814. At polygon 816, the classifier model is trained using the training projected vectors (i.e., the training vectors that originated from the highlighted parse trees). Specifically, for example, the "true" mathematical vectors from polygon 810 can be used as positive training examples, and the "false" mathematical vectors from polygon 810 can be used as negative training examples. At polygon 818, the highlighted parse trees can also be classified using the classifier model so that the NLP learning machine can compare the classification of each node to the highlighting (or lack thereof) of each node to see how often they match. Then the classifier model can then be adjusted in order to increase the number of matches of the classification with the highlighting. Thereby, the classifier model is be improved through machine learning. This training process is performed with the NLP learning machine being off-line, and method 800 ends at polygon 820.

The features of method 800 allow for an NLP learning machine to be trained to find spans (e.g., hypothetical spans) in natural language text. This can be done using a relatively small number of labeled spans and a relatively large number of unlabeled spans, which increases the effectiveness of the NLP learning machine compared to only using the labeled spans. However, naturally, the unlabeled spans do not require all of the time and effort that labeling spans requires, but the disclosed NLP learning machine (including the projection model) can use the unlabeled spans to amplify the effect of learning from the labeled spans. In addition, since there is no clipping of nodes from the initial consideration table-making (i.e., at polygon 806), nodes that are not directly related to known span-member nodes (e.g., sibling nodes) are still analyzed. But since there is the checking for highlighting of target nodes and labeling spans "true" or "false" later on in the process (i.e., at polygon 816), NLP learning machine can still learn to clip nodes that do not belong in the span being created. Moreover, the analysis is done without the use of numerous complicated blocklist and allowlist rows that must be contrived and then maintained. In addition, in the situation where incomplete blocklists and/or allowlists are supplied for clipping, an NLP learning machine trained according to method 800 can use its knowledge of clipping by context to fall back on instead of relying on the lists.

In some embodiments, method 800 further includes polygon 822. This is denoted by the phantom arrows that extends from polygon 810 to polygon 822 and from polygon 822 to polygon 812. In such an embodiment, method 800 would progress through polygon 822 instead of moving from polygon 810 directly to polygon 812. At polygon 822, a feature selection is made based on the analysis of the labeled spans, for example, based Chi-squared analysis and/or signal-to-noise ratio analysis. A feature selection may indicate which columns of the training encoded vectors are more strongly predictive of a particular problem being solved (for example, finding hypothetical or negated spans in new, unlabeled text). However, the feature selection for hypothetical spans can differ from the feature selection for negated spans. Therefore, the feature selection can be further narrowed based on the answer being sought (for example, finding hypothetical spans or finding negated spans). Selecting a feature may allow deletion of some of the columns (i.e., some of the text) because they may not be as predictive of the solution to the problem. For example, certain columns of the training encoded vectors may be removed prior to training the projection model at polygon 812 in order to find hypothetical spans.

In this alternate embodiment, the feature selection is set before the projection model is trained at polygon 812. This is so that the projection model will be more attuned to what the sought-after answer is. This can increase the accuracy with which results are obtained. However, if the desired answer is changed, then the projection model may need to be retrained to be better attuned to the new sought-after answer. If the data set used for learning is relatively small, then retraining may not be a large undertaking. But if the learning data set is large, then a more general learning approach that does not include polygon 822 may be beneficial because it would not need retraining (despite the possibility that it would not be as accurate in its predictions).

Figure 9:
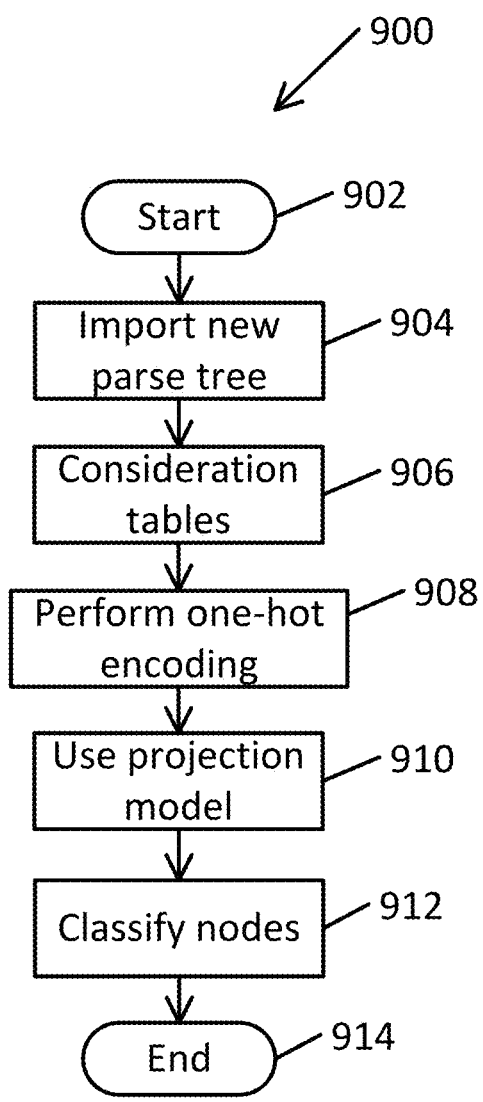
FIG. 9 is a flowchart of an NLP learning machine operating on natural language text.

FIG. 9 is a flowchart of method 900 of an NLP learning machine operating on natural language text that starts at polygon 902. At polygon 904, the NLP learning machine imports a new series of natural language text (e.g., a sentence) which is converted into a new parse tree. At polygon 906 (which can be similar to polygon 806 in FIG. 8), new consideration tables are made from every possible traversal in the new parse tree such that every new node-target pair has a table. At polygon 908 (which can be similar to polygon 810 in FIG. 8), the new consideration tables are one-hot encoded, and at polygon 910 (which can be similar to polygon 814 in FIG. 8), the new encoded vectors are processed using the projection model. At polygon 912, the nodes from the new text are classified as being in a sought-after type of span or not, and the NLP learning machine can provide an output, for example, a highlighted span that indicates which nodes are members of that span. Then method 900 ends at polygon 914. Thereby, using method 900, an NLP learning machine can operate online on new text from real-world sources (not shown), for example, to determine factual passages from hypothetical passages.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of using a natural language processor, the method comprising:
 importing a highlighted training text including a first plurality of training nodes;
 importing a non-highlighted training text including a second plurality of training nodes;
 enhanced-one-hot encoding the highlighted and non-highlighted training text, wherein
  enhanced-one-hot encoding comprises:
  generating a parse tree having a plurality of nodes; and
  generating a vector table that includes a first row and a second row, wherein:
   the first row represents a first traversal through the parse tree from a trigger node to a first target node, wherein the trigger node includes a first attribute and a second attribute, and wherein the first target node includes a third attribute and a fourth attribute; and
   the second row represents a second traversal through the parse tree from the trigger node to a second target node, wherein the second target node includes a fifth attribute and a sixth attribute;

wherein the column headings of the vector table comprise a plurality of attributes including the first attribute, the second attribute, the third attribute, the fourth attribute, the fifth attribute, and the sixth attribute;

wherein each position in the first row of the vector table includes a "1" for each column heading that is true for the first traversal; and wherein each position in the first row of the vector table includes a "0" for each column heading that is false for the first traversal;

training a projection model using the highlighted and non-highlighted training text;

processing the highlighted training text using the projection model;

training a classifier model using the highlighted processed training text;

importing new text including a plurality of new nodes;

enhanced-one-hot encoding the new text;

processing the new text using the projection model; and determining, using the classifier model, whether one of the plurality of new nodes is in a sought-after class.

2. The method of claim 1, wherein the sought-after class is members of a hypothetical text span.

3. The method of claim 1, further comprising:
outputting a highlighted new text that indicates each of the plurality of new nodes is in the sought-after class.

4. The method of claim 1, further comprising:
training an enhanced-one-hot encoder using the highlighted and non-highlighted training text.

5. The method of claim 1, wherein the enhanced-one-hot encoding the highlighted training text generates highlighted training vectors that are then processed using the projection model, the method further comprising:

processing the highlighted processed training vectors using the classifier model to determine whether each node is in the sought-after class;

comparing the determinations of whether each node is in the sought-after class with the highlighting of each node; and adjusting the classifier model to increase the number of determinations that are the same as the highlighting.

6. The method of claim 1, further comprising:
making a feature selection; and
removing a node from the highlighted and non-highlighted training text, based on the feature selection, prior to training the projection model.

7. A method of training a natural language processor, the method comprising:

importing a highlighted training text including a first plurality of training nodes;

importing a non-highlighted training text including a second plurality of training nodes;

converting the highlighted training text into highlighted training conversion tables;

converting the non-highlighted training text non-highlighted training conversion tables;

training an enhanced-one-hot encoder using the highlighted and non-highlighted training conversion tables;

enhanced-one-hot encoding the highlighted training conversion tables to generate highlighted training vectors;

enhanced-one-hot encoding the non-highlighted conversion tables to generate non-highlighted training vectors, wherein enhanced-one-hot encoding comprises:
generating a parse tree having a plurality of nodes; and generating a vector table that includes a first row and a second row, wherein:

the first row represents a first traversal through the parse tree from a trigger node to a first target node, wherein the trigger node includes a first attribute and a second attribute, and wherein the first target node includes a third attribute and a fourth attribute; and the second row represents a second traversal through the parse tree from the trigger node to a second target node, wherein the second target node includes a fifth attribute and a sixth attribute;

wherein the column headings of the vector table comprise a plurality of attributes including the first attribute, the second attribute, the third attribute, the fourth attribute, the fifth attribute, and the sixth attribute;

wherein each position in the first row of the vector table includes a "1" for each column heading that is true for the first traversal; and wherein each position in the first row of the vector table includes a "0" for each column heading that is false for the first traversal;

training a projection model using the highlighted and non-highlighted training vectors;

processing the highlighted training vectors using the projection model to generate highlighted processed training vectors; and training a classifier model using the highlighted processed training vectors, wherein the classifier model determines whether a node is in a sought-after class.

8. The method of claim 7, wherein the sought-after class is members of a hypothetical text span or members of a factual text span.

9. The method of claim 7, further comprising:
converting the highlighted training text into highlighted parse trees; and
converting the non-highlighted training text into non-highlighted parse trees.

10. The method of claim 7, further comprising:
processing the highlighted processed training vectors using the classifier model to determine whether each node is in the sought-after class;
comparing determinations using the classifier model of whether each node is in the sought-after class with the highlighting of each node; and
adjusting the classifier model to increase the number of determinations that are the same as the highlighting.

11. The method of claim 7, further comprising:
making a feature selection; and
removing a column from the highlighted and non-highlighted training vectors, based on the feature selection, prior to training the projection model.

12. A system to find nodes in a span, the system comprising:
a plurality of highlighted parse trees representing labeled natural language text;
a plurality of non-highlighted parse trees representing unlabeled natural language text;
a new parse tree representing new natural language text;
a natural language processing (NLP) learning machine configured to process the plurality of highlighted parse trees, the plurality of non-highlighted parse trees, and the new parse tree, wherein the NLP learning machine includes a computing processor; and a memory coupled to the computing processor, wherein the memory comprises instructions which, when executed by the computing processor, specifically configures the computing processor and causes the computing processor to:
import a highlighted training text including a first plurality of training nodes;
import a non-highlighted training text including a second plurality of training nodes;
enhanced-one-hot encode the highlighted and non-highlighted training text, wherein enhanced-one-hot encoding comprises:
generating a parse tree having a plurality of nodes; and
generating a vector table that includes a first row and a second row, wherein:
the first row represents a first traversal through the parse tree from a trigger node to a first target node, wherein the trigger node includes a first attribute and a second attribute, and wherein the first target node includes a third attribute and a fourth attribute; and
the second row represents a second traversal through the parse tree from the trigger node to a second target node, wherein the second target node includes a fifth attribute and a sixth attribute;
wherein the column headings of the vector table comprise a plurality of attributes including the first attribute, the second attribute, the third attribute, the fourth attribute, the fifth attribute, and the sixth attribute;
wherein each position in the first row of the vector table includes a "1" for each column heading that is true for the first traversal; and
wherein each position in the first row of the vector table includes a "0" for each column heading that is false for the first traversal;
train a projection model using the highlighted and non-highlighted training text;
processing the highlighted training text using the projection model;
train a classifier model using the highlighted processed training text;
import new text including a plurality of new nodes;
enhanced-one-hot encode the new text;
process the new text using the projection model; and
determine, using the classifier model, whether one of the plurality of new nodes is in a sought-after class.

13. The system of claim 12, wherein the sought-after class is members of a hypothetical text span.

14. The system of claim 12, wherein the memory further comprises instructions which, when executed by the computing processor, specifically configures the computing processor and causes the computing processor to:
output a highlighted new text that indicates each of the plurality of new nodes is in the sought-after class.

15. The system of claim 12, wherein the memory further comprises instructions which, when executed by the computing processor, specifically configures the computing processor and causes the computing processor to:
train an enhanced-one-hot encoder using the highlighted and non-highlighted training text.

16. The system of claim 12, wherein the enhanced-one-hot encoding the highlighted training text generates highlighted training vectors that are then processed using the projection model, and wherein the memory further comprises instructions which, when executed by the computing processor, specifically configures the computing processor and causes the computing processor to:
process the highlighted processed training vectors using the classifier model to determine whether each node is in the sought-after class;
compare the determinations of whether each node is in the sought-after class with the highlighting of each node; and
adjust the classifier model to increase the number of determinations that are the same as the highlighting.

17. The system of claim 12, wherein the memory further comprises instructions which, when executed by the computing processor, specifically configures the computing processor and causes the computing processor to:
make a feature selection; and
remove a node from the highlighted and non-highlighted training text, based on the feature selection, prior to training the projection model.

18. A system to find nodes in a span, the system comprising:
a plurality of highlighted parse trees representing labeled natural language text;
a plurality of non-highlighted parse trees representing unlabeled natural language text;
a new parse tree representing new natural language text;
a natural language processing (NLP) learning machine configured to process the plurality of highlighted parse trees, the plurality of non-highlighted parse trees, and the new parse tree, wherein the NLP learning machine includes a computing processor;
and a memory coupled to the computing processor, wherein the memory comprises instructions which, when executed by the computing processor, specifically configures the computing processor and causes the computing processor to:
convert the highlighted training text into highlighted training conversion tables;
convert the non-highlighted training text non-highlighted training conversion tables;
train an enhanced-one-hot encoder using the highlighted and non-highlighted training conversion tables;
enhanced-one-hot encode the highlighted training conversion tables to generate highlighted training vectors, wherein enhanced-one-hot encoding comprises:
generating the new parse tree having a plurality of nodes; and
generating a vector table that includes a first row and a second row, wherein:
the first row represents a first traversal through the new parse tree from a trigger node to a first target node, wherein the trigger node includes
a first attribute and a second attribute, and wherein the first target node includes a third attribute and a fourth attribute; and
the second row represents a second traversal through the new parse tree from the trigger node to a second target node, wherein the second target node includes a fifth attribute and a sixth attribute;
wherein the column headings of the vector table comprise a plurality of attributes including the first attribute, the second attribute, the third attribute, the fourth attribute, the fifth attribute, and the sixth attribute;
wherein each position in the first row of the vector table includes a "1" for each column heading that is true for the first traversal; and wherein each position in the first row of the vector table includes a "0" for each column heading that is false for the first traversal;
enhanced-one-hot encode the non-highlighted conversion tables to generate non-highlighted training vectors,
train a projection model using the highlighted and non-highlighted training vectors;
process the highlighted training vectors using the projection model to generate highlighted processed training vectors; and
train a classifier model using the highlighted processed training vectors,
wherein the classifier model determines whether a node is in a sought-after class.

19. The system of claim 18, wherein the sought-after class is members of a hypothetical text span or members of a factual text span.

20. The system of claim 18, wherein the memory further comprises instructions which, when executed by the computing processor, specifically configures the computing processor and causes the computing processor to:
convert the highlighted training text into highlighted parse trees; and
convert the non-highlighted training text into non-highlighted parse trees.

21. The system of claim 18, wherein the memory comprises instructions which, when executed by the computing processor, specifically configures the computing processor and causes the computing processor to:
process the highlighted processed training vectors using the classifier model to determine whether each node is in the sought-after class;
compare determinations using the classifier model of whether each node is in the sought-after class with the highlighting of each node; and
adjust the classifier model to increase the number of determinations that are the same as the highlighting.

22. The system of claim 18, wherein the memory comprises instructions which, when executed by the computing processor, specifically configures the computing processor and causes the computing processor to:
make a feature selection; and
remove a column from the highlighted and non-highlighted training vectors, based on the feature selection, prior to training the projection model.

23. A computer program product comprising a computer readable storage medium having a computer readable program stored therein to find nodes in a span, wherein the computer readable program, when executed on a computing device, specifically configures the computing device, and causes the computing device to:
import a highlighted training text including a first plurality of training nodes;
import a non-highlighted training text including a second plurality of training nodes;
enhanced-one-hot encode the highlighted and non-highlighted training text, wherein enhanced-one-hot encoding comprises:
generating a parse tree having a plurality of nodes; and
generating a vector table that includes a first row and a second row, wherein:
the first row represents a first traversal through the parse tree from a trigger node to a first target node, wherein the trigger node includes a first attribute and a second attribute, and wherein the first target node includes a third attribute and a fourth attribute; and
the second row represents a second traversal through the parse tree from the trigger node to a second target node, wherein the second target node includes a fifth attribute and a sixth attribute;
wherein the column headings of the vector table comprise a plurality of attributes including the first attribute, the second attribute, the third attribute, the fourth attribute, the fifth attribute, and the sixth attribute;
wherein each position in the first row of the vector table includes a "1" for each column heading that is true for the first traversal; and
wherein each position in the first row of the vector table includes a "0" for each column heading that is false for the first traversal;
train a projection model using the highlighted and non-highlighted training text;
processing the highlighted training text using the projection model;
train a classifier model using the highlighted processed training text;
import new text including a plurality of new nodes;
enhanced-one-hot encode the new text;
process the new text using the projection model; and
determine, using the classifier model, whether one of the plurality of new nodes is in a sought-after class.

24. The method of claim 23, wherein the sought-after class is members of a hypothetical text span.

25. The method of claim 23, wherein the computer readable program further, when executed on a computing device, specifically configures the computing device, and causes the computing device to:
make a feature selection; and
remove a node from the highlighted and non-highlighted training text, based on the feature selection, prior to training the projection model.

* * * * *